US009395425B2

(12) United States Patent
Diamond et al.

(10) Patent No.: US 9,395,425 B2
(45) Date of Patent: Jul. 19, 2016

(54) METHOD AND APPARATUS FOR MAGNETIC SUSCEPTIBILITY TOMOGRAPHY, MAGNETOENCEPHALOGRAPHY, AND TAGGANT OR CONTRAST AGENT DETECTION

(71) Applicant: The Trustees of Dartmouth College, Hanover, NH (US)

(72) Inventors: Solomon G. Diamond, Hanover, NH (US); Broc A. Burke, St. Louis, MO (US); Bradley W. Ficko, West Lebanon, NH (US)

(73) Assignee: THE TRUSTEES OF DARTMOUTH COLLEGE, Hanover, NH (US)

( * ) Notice: Subject to any disclaimer, the term of this patent is extended or adjusted under 35 U.S.C. 154(b) by 0 days.

(21) Appl. No.: 14/420,828

(22) PCT Filed: Aug. 23, 2013

(86) PCT No.: PCT/US2013/056436
§ 371 (c)(1),
(2) Date: Feb. 10, 2015

(87) PCT Pub. No.: WO2014/031985
PCT Pub. Date: Feb. 27, 2014

(65) Prior Publication Data
US 2015/0219732 A1    Aug. 6, 2015

Related U.S. Application Data

(60) Provisional application No. 61/693,044, filed on Aug. 24, 2012.

(51) Int. Cl.
*G01R 33/16* (2006.01)
*G01R 33/48* (2006.01)
(Continued)

(52) U.S. Cl.
CPC .............. *G01R 33/16* (2013.01); *A61B 5/0042* (2013.01); *A61B 5/04008* (2013.01); *A61B 5/0522* (2013.01); *G01N 27/72* (2013.01); *A61B 2562/0223* (2013.01)

(58) Field of Classification Search
CPC ........................................................ G01R 33/16
USPC .......................................................... 324/201
See application file for complete search history.

(56) References Cited

U.S. PATENT DOCUMENTS 5,622,169 A    4/1997 Golden et al.
2009/0143665 A1    6/2009 Seki et al.
(Continued)

FOREIGN PATENT DOCUMENTS

WO    2014031985 A1    2/2014

OTHER PUBLICATIONS

PCT Patent Application PCT/US2013/056436 International Search Report and Written Opinion issued Nov. 27, 2013, 12 pages.
(Continued)

*Primary Examiner* — Bot Ledynh
(74) *Attorney, Agent, or Firm* — Lathrop & Gage LLP

(57) ABSTRACT

A magnetic susceptibility tomographic device has sensitive magnetic sensors about a measurement volume and AC bias coils for providing magnetic fields within the volume. Sensing circuitry reads the sensors, and a processor executes magnetic susceptibility tomography (MST) routines from memory to divide the measurement volume into voxels, to determine differences between applied and measured field strengths of magnetic fields at each voxel and thereby determines magnetic susceptibility of each voxel, and to construct tomographic images representative of magnetic susceptibility as MST images. Embodiments with SQUID and fluxgate sensors are described. Applications to direct measurement of tissue magnetic susceptibility, and to locating and quantifying tagged magnetic nanoparticles are disclosed, including antibody-tagged nanoparticles for use in cancer diagnosis and treatments, and the retrieval of taggant identification codes from an object.

43 Claims, 12 Drawing Sheets

(51) Int. Cl.
*A61B 5/04* (2006.01)
*A61B 5/05* (2006.01)
*G01N 27/72* (2006.01)
*A61B 5/00* (2006.01)

(56) References Cited

U.S. PATENT DOCUMENTS

2010/0219825 A1 9/2010 Sato et al.
2011/0089942 A1 4/2011 Goodwill et al.
2011/0182821 A1 7/2011 Gruell et al.
2012/0119739 A1 5/2012 Gleich
2012/0153949 A1 6/2012 Biederer et al.
2012/0194198 A1 8/2012 Moran

OTHER PUBLICATIONS

PCT Patent Application PCT/US15/29481 International Search Report and Written Opinion dated Aug. 13, 2015, 8 pages.

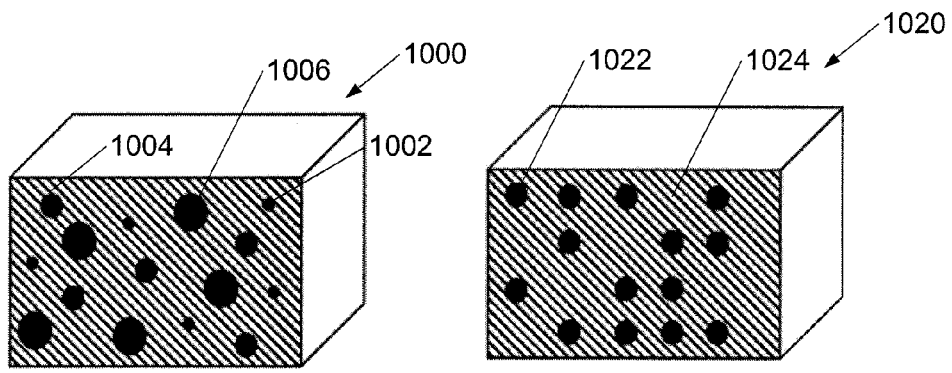
Fig. 11A
Nanoparticle taggant encoding based on size distribution
Fig. 11B
Nanoparticle taggant encoding based on spatial patterning
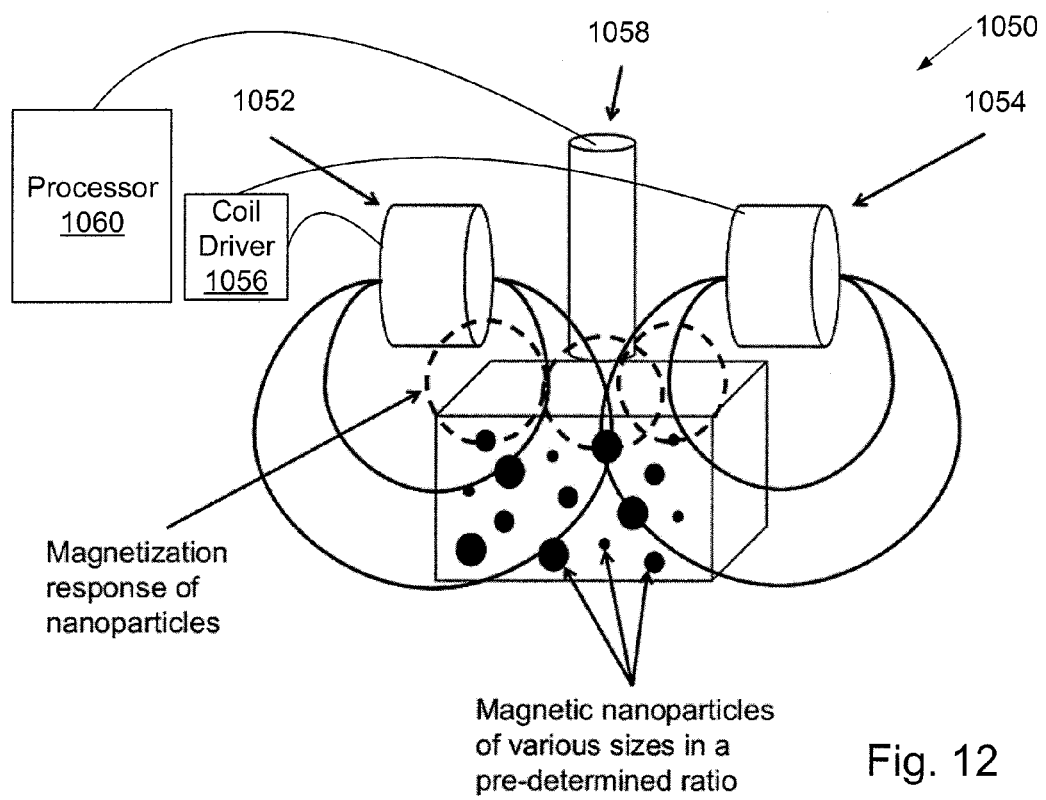
Fig. 12

METHOD AND APPARATUS FOR MAGNETIC SUSCEPTIBILITY TOMOGRAPHY, MAGNETOENCEPHALOGRAPHY, AND TAGGANT OR CONTRAST AGENT DETECTION

RELATED APPLICATIONS

This application claims priority to U.S. Patent Application Ser. No. 61/693,044, filed Aug. 24, 2013, the disclosure of which is incorporated herein by reference.

GOVERNMENT INTEREST

The invention was made with support of the National Institutes of Health, National Cancer Institute grants 1R21EB016241-01A1, 1U54CA151662-01, and 5R24HD065703-03. The government has certina rights in the invention.

FIELD

The present document relates to nondestructive imaging of magnetically susceptible materials and biologically-generated magnetic fields. The magnetic susceptibility imaging described relates to noninvasive functional neuroimaging, imaging of magnetic nanoparticles, Magnetic Susceptibility Tomography (MST) and Magnetoencephalography (MEG), magnetically susceptible taggant technologies, and other applications that require measurement of, and detection of minute changes in, magnetic susceptibility.

BACKGROUND

Measurement and mapping of human brain neural activity is of interest in medicine, neuroscience and psychology. Prior techniques of noninvasively measuring and mapping neural activity in the brain, such as electroencephalography (EEG) and magnetoencephalography (MEG) have been used both as research tools and for clinical diagnosis. Indirect methods of imaging neural activity measure tissue metabolism with positron emission tomography (PET) and single photon emission computed tomography (SPECT), or via the hemodynamic response measured with functional magnetic resonance imaging (fMRI) and functional near infrared spectroscopy (fNIRS) neuroimaging.

A direct noninvasive approach to measuring neuronal activity is with electroencephalography (EEG), however it can be difficult to interpret the waveforms of signal versus time plotted at various electrode locations on a subject's skull that are produced by traditional electroencephalographs. Electroencephalography uses electrodes placed in contact with the scalp to detect electric voltages generated by large groups of firing neurons within the brain, and is of use in diagnosis of epilepsy and other disorders of the brain.

Another noninvasive approach to measuring neuronal activity is magnetoencephalography (MEG) that measures magnetic fields produced by the brain. Commercial magnetoencephalography machines that sense and map the minute magnetic fields associated with the electric voltages and currents generated by large groups of firing neurons within the brain, and construct a three-dimensional map of detected neural activity, are available from companies such as Elekta AB, Stockholm, Sweden. In addition to magnetoencephalographic magnetic fields, biomagnetic fields also include magnetic fields generated by muscular activity, including muscular activity of the heart and intestines.

The dominant functional neuroimaging modality today is fMRI using blood-oxygen-level-dependent (BOLD) contrast to reconstruct three-dimensional movies of brain activity.

fNIRS (functional Near Infrared Spectrometry) is an alternative method of measuring hemodynamic responses near the surface of the brain, and which does not require the intense magnetic field and massive, immobile, magnets of fMRI. Because fNIRS relies on reconstruction of scatterers and absorbers of infrared light penetrating the brain, fNIRS does not well resolve activity in deep structures.

The hemodynamic response measured by fNIRS and fMRI is a localized change in blood flow, blood volume, and blood oxygenation that is coupled to neural activity by the activity of astrocytes, neurotransmitter signaling, and metabolites in the tissue. This neurovascular coupling involves a complex interplay of neuron activity and spatiotemporal variations in metabolism, blood flow and blood oxygen level. These processes are functionally connected in neurovascular units of the brain, which are composed of integrated networks of neurons, astrocytes, and vascular smooth muscle cells.

Combined multimodal measurement of neural and hemodynamic responses is preferred for studies of central nervous system (CNS) diseases and investigations where neurovascular coupling is questioned Impaired neurovascular coupling is implicated in stroke, hypertension, epilepsy, brain tumors, Alzheimer's and Parkinson's diseases and is the subject of intense biomedical research on brain dynamics. The available noninvasive neuroimaging instruments measure only one physiological process, i.e., neural, metabolic, or hemodynamic. Studies on neurovascular coupling currently require simultaneous operation of two neuroimaging modalities and typically suffer from mismatched resolution, mismatched data rates, and noise interference between the measurement modalities, e.g., combined fMRI and EEG.

Noninvasive imaging of magnetic nanoparticles is another, related, health-related field of interest. The magnetic properties of iron-core nanoparticles have opened new avenues of targeted cancer therapy, where they are used to selectively heat and kill tumor cells. Effective technology for noninvasive, in vivo, detection and location of magnetic nanoparticles is essential to the development and implementation of this targeted cancer therapy.

Hyperthermia treatment of cancerous tumors can effectively cause cancer cell death through mechanisms of protein denaturation and/or rupture of the cellular membrane. The destroyed cancer cells are then removed by macrophages, causing the tumor to shrink.

It is critically important in hyperthermia therapy to specifically target the cancer cells with the heat deposition and to minimize harm to healthy and/or critical tissues. Targeted hyperthermia therapy typically relies on localizing an energy-absorbing agent within the tumor prior to application of energy to the region. A variety of specific nanoparticles have been designed for this purpose. One approach is to coat the nanoparticles with gold and then to deposit energy with laser light.

Another approach is to use nanoparticles having an iron or iron-oxide component. In embodiments, the iron or iron-oxide component may be a core, or shell surrounding a core of another material. The iron or iron-oxide component gives these nanoparticles a high level of magnetic susceptibility. Since nanoparticles having such an iron or iron-oxide component typically have other materials surrounding the iron or iron-oxide component—such as biocompatible coatings and/or tissue-binding antibodies or agents—these nanoparticles are referred to herein as iron-core nanoparticles. Alternating magnetic fields are then used to selectively heat the magnetic nanoparticles in the tumor.

The exteriors of nanoparticles can also be modified to contain cancer-binding molecules that can selectively bind cancer cells and thereby deliver nanoparticles to cancerous cells. Several cancer-specific antibodies that can be conjugated to nanoparticles have already been approved by the Food and Drug Administration (FDA) and are clinically used to treat tumors. Cancer types that can be targeted in this way currently include colorectal, non-small cell lung, breast, leukemia, gastrointestinal, myeloma, lymphoma, kidney, and liver. Nanoparticles have also been engineered to target atherosclerotic plaques—which are of importance in heart disease and stroke—and Alzheimer's plaques. Iron-core nanoparticles can be used to target an increasingly wide range of diseases. These targeting mechanisms impart enhanced magnetic susceptibility to the targeted tumor region, and can be used both for treatment and for tumor localization and identification.

The magnetic susceptibility property of iron-core nanoparticles can also be used in conjunction with bound disease-targeting molecules, such as antibodies, for the detection of the diseased tissue in disease diagnostics. For example, the increased magnetic susceptibility of tissue tagged with nanoparticles will alter the contrast of images taken with MRI, or dyes delivered by nanoparticles, could be used to obtain enhanced contrast with NIRS. Imaging of iron-core nanoparticle locations is also important when using targeted chemotherapy and targeted hyperthermia treatments because damage to vital tissues and structures could result if the particles are in the wrong location when activated with the external energy.

Another related field is labeling, and reading of labels, of materials and manufactured parts for the purposes of authentication, track and trace, and supply chain management.

The problem of counterfeit electronic parts is a major problem in the Department of Defense (DOD) supply chain, as well as commercial aviation and drug supplies.

SUMMARY

A magnetic susceptibility tomographic device has sensitive magnetic sensors about a measurement volume and AC bias coils for providing magnetic fields within the volume. Sensing circuitry reads the sensors, and a processor executes magnetic susceptibility tomography (MST) routines from memory to divide the measurement volume into voxels, to determine differences between applied and measured field strengths of magnetic fields at each voxel and thereby determines magnetic susceptibility of each voxel, and to construct tomographic images representative of magnetic susceptibility as MST images. Embodiments with SQUID and fluxgate sensors are described. Applications to direct measurement of tissue magnetic susceptibility, and to locating and quantifying tagged magnetic nanoparticles are disclosed, including antibody-tagged nanoparticles for use in cancer diagnosis and treatments.

In an embodiment, an apparatus for obtaining magnetic susceptibility data includes multiple sensitive magnetic sensors disposed about a measurement volume, and adapted to measure magnetic fields of the measurement volume; multiple bias coils disposed about the measurement volume and adapted for providing magnetic fields within the measurement volume; driving circuitry coupled to the bias coils and adapted to driving the bias coils with alternating current; sensing circuitry coupled to read the sensitive magnetic sensors; digitization circuitry adapted to digitize readings of the sensitive magnetic sensors; a processor adapted to receive information from the digitization circuitry; magnetic susceptibility tomography (MST) routines in memory of the processor, the MST routines comprising machine readable instructions for directing the processor to divide the measurement volume into voxels, to determine differences between applied and measured field strengths of magnetic fields at each sensor, to determine a value at each voxel selected from the group consisting of a contribution of difference between applied and measured strengths of magnetic fields and a magnetic susceptibility, and to construct tomographic images based on those values as MST images.

In an alternative embodiment, a method of producing magnetic susceptibility tomographic (MST) images of an object includes providing an alternating magnetic field to a volume of an object from at least a first bias coil at a first frequency, a second bias coil at a second frequency, a third bias coil at a third frequency, and a fourth bias coil at a fourth frequency, the first, second, third, and fourth frequencies being different; measuring magnetic fields at a plurality of sensors disposed about the volume; constructing a model in memory of a processor, the model having multiple voxels representative of smaller volumes within the volume; correlating currents of the bias coils to measured magnetic fields at each sensor of the plurality of sensors to determine an applied and an induced magnetic field at each sensor; deriving magnetic susceptibility information for each voxel; and producing an MST image indicative of magnetic susceptibility at voxels.

In an alternative embodiment, an apparatus for obtaining magnetic susceptibility data from an object including a plurality of sensitive magnetic sensors disposed about the object, and adapted to measure magnetic fields of the object; a plurality of bias coils disposed about the object and adapted for providing magnetic fields within the object; driving circuitry coupled to the bias coils and adapted to driving the bias coils with alternating current; sensing circuitry coupled to read the sensitive magnetic sensors; digitization circuitry adapted to digitize readings of the sensitive magnetic sensors; a processor adapted to receive information from the digitization circuitry; magnetic susceptibility taggant recognition (MSTR) routines in memory of the processor, the MSTR routines comprising machine readable instructions that when executed determine differences between applied and measured field strengths of magnetic fields at each sensor, to determine a response comprising a contribution of difference between applied and measured strengths of magnetic fields at a plurality of frequencies and a frequency distribution of magnetic susceptibility, and to recognize a taggant in the object when the response meets predetermined criteria.

BRIEF DESCRIPTION OF THE FIGURES

FIG. 11A is a schematic diagram of an object tagged with a particular size distribution of nanoparticles.

FIG. 11B is a schematic diagram of an object tagged with a particular spatial distribution of nanoparticles.

FIG. 12 is a schematic representation of a simplified detection and particle-size-distribution detection device for nanoparticles in an object tagged with a nanoparticle size distribution according to FIG. 11A.

DETAILED DESCRIPTION OF THE EMBODIMENTS

Use for Imaging

Figure 1A:
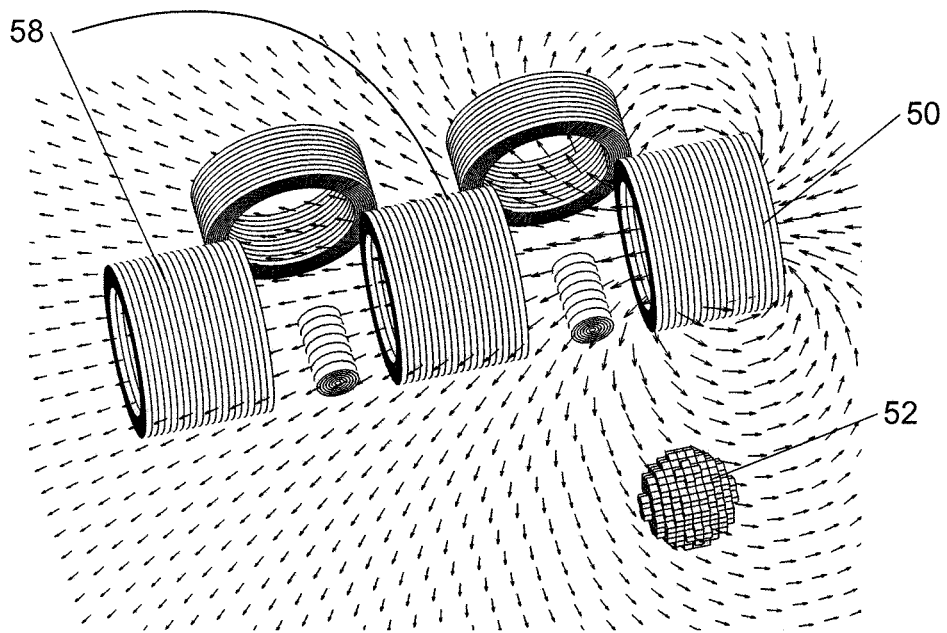
FIG. 1A illustrates an applied field to a magnetically susceptible material.

The present device and method provides for near-simultaneously measuring intrinsic neural (MEG) and hemodynamic activity (MST) without any need for a contrast injection and can do so with high temporal and spatial resolution. The device and method solves the substantial technical problem of integrating two capabilities of the superconducting quantum interference device (SQUID) system and/or atomic magnetometer system: biomagnetometer measurement of magnetic susceptibility (MST) and magnetoencephalography (MEG). Measuring neural activity with MEG is based on detecting the magnetic fields produced by active neurons. SQUID susceptibility measurement detects changes in the level of deoxygenated hemoglobin in the blood, similarly to fMRI, but with faster temporal sampling. By implementing magnetic susceptibility measurement of hemodynamics with alternating current (AC) modulation at high frequencies, lock-in amplifier and applied magnetic field compensation techniques may be used for the hemodynamic measurement and the hemodynamic measurement does not interfere with a simultaneous MEG measurement. This device and method enables high precision, high-resolution multimodal neuroimaging for scientific and medical applications of noninvasive imaging of neurovascular brain dynamics.

Injection of magnetic nanoparticles, which may in some embodiments be antibody-tagged, gives enhanced contrast to the tissue that contains the nanoparticles in the susceptometry device and method. These particles may be modified to bind specifically to certain biological tissues such as tumors. Due to the high magnetic susceptibility contrast from the surrounding tissue, the magnetic nanoparticles may also be detected and imaged with a fluxgate magnetometer-based susceptometer that utilizes a similar AC bias field and tomographic reconstruction algorithms. The fluxgate-susceptometer could be a fixed frame instrument or a portable hand-held imager that is far smaller and far less expensive than SQUID-based machines because the fluxgate also does not require use of cryogenic cooling, and does not require a magnetically shielded room. An atomic magnetometer has low-noise properties and exquisite sensitivity comparable to a SQUID sensor but does not require cryogenic cooling. Achieving the lowest possible noise measurements with a SQUID or atomic magnetometer requires use of a magnetically shielded room. Atomic magnetometers and fluxgates will operate outside of a magnetically shielded room, but with greater noise from the environment that may overwhelm MEG signals while possibly allowing detection of MST signals.

A magnetic susceptibility tomographic device has sensitive magnetic sensors about a measurement volume and AC bias coils for providing magnetic fields within the volume. Magnetic field compensation coils reduce the field bias at the sensors to reduce the dynamic range requirements of the sensor electronics. Sensing circuitry reads the sensors, and a processor executes magnetic susceptibility tomography (MST) routines from memory to divide the measurement volume into voxels, to determine differences between applied and measured field strengths of magnetic fields at each sensor, and to then determine a contribution of difference between applied and measured field strength, or a magnetic susceptibility, at each voxel, and to construct tomographic images displaying difference between applied and measured field strength, or magnetic susceptibility, at multiple voxels as MST images. MST images may be reconstructed in three-dimensional space or as two-dimensional topographic images.

A method of producing magnetic susceptibility tomographic (MST) images of a subject includes providing an alternating magnetic field to a volume of a subject from two or more bias coils each modulated at a separate frequency. Magnetic fields at each of several sensors disposed about the volume are measured, and currents of the bias coils are correlated to measured magnetic fields at each sensor of the plurality of sensors to determine an applied and an induced magnetic field measured at each sensor from each bias coil. The magnetic susceptibility at each voxel is then derived and displayed as an MST image.

Figure 1B:
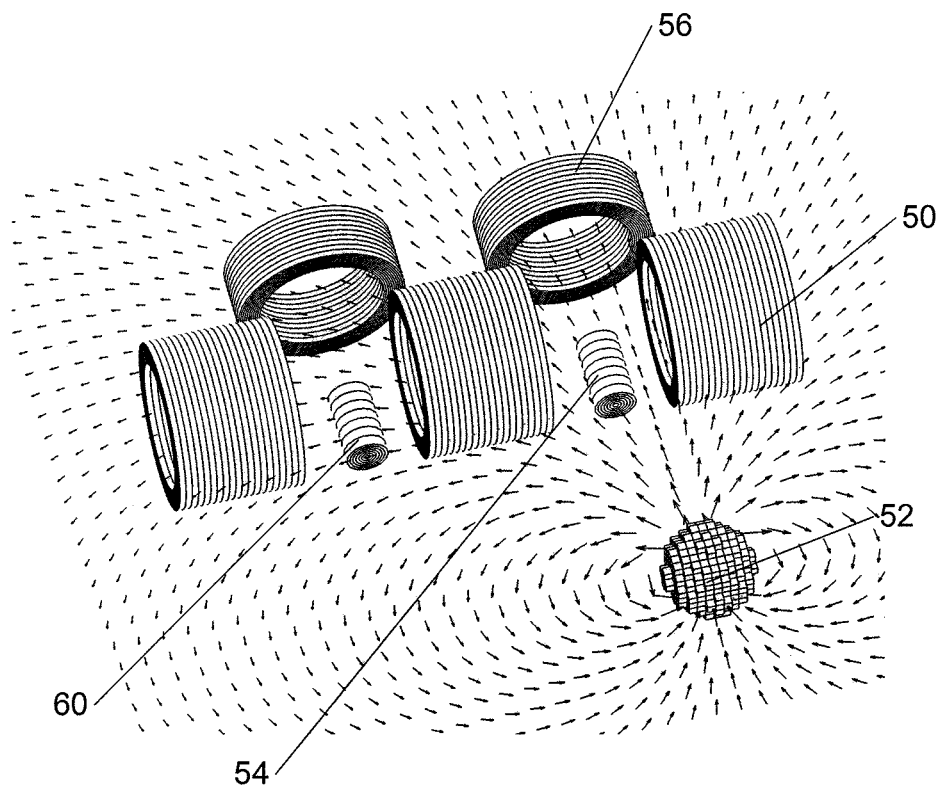
FIG. 1B illustrates sensing a field developed in the magnetically susceptible material while a bias field is applied.

FIG. 1A illustrates an applied field, provided by bias magnet 50, to a magnetically susceptible material 52. This field induces a field in the material 52. FIG. 1B illustrates sensing a field developed in the magnetically susceptible material 52 using a sensor 54 while the bias-magnet field is applied. In a particular embodiment, as illustrated in FIG. 1E, the bias-magnet field is nulled at sensor 54 by compensation coils 56 such that fields at sensor 54 are perpendicular to an axis of sensitivity of sensor 54, and thus ignored by sensor 54 in the absence of an induced field from material 52. An apparatus having an array of bias magnets 50, 58, and multiple sensors 60, 54, is capable of imaging by sensing magnetically susceptible material at more than one location; while imaging response of magnetically susceptible material at separate locations in a subject is distinguished by selectively energizing bias magnets 50, 58, and reading selected sensors 54, 60.

Use for Tagging

The present devices and method also provides the use of nanoparticle labeling and scanning of materials and manufactured parts for the purposes of authentication, track and trace, and supply chain management. In this invention, nanoparticles are embedded in and/or on a part during the manufacturing process and later scanned by a susceptibility-imaging device to retrieve the information contained in these nanoparticles.

The information contained in these nanoparticles could be imparted in several ways. One method is a blend of different size distributions and concentrations of nanoparticles that are mixed uniformly into a material. This combination could then be scanned by a susceptometer capable of spectroscopic analysis based on the amplitude and phase response of the magnetic nanoparticles as a function of frequency. The spectroscopic analysis would reveal the particular nanoparticle signature embedded in the material. Another method of embedding information contained in nanoparticle is spatial encoding of nanoparticles throughout the material or part. This spatial encoding would represent information in a 3-dimensional spatial pattern. Information could then be retrieved by a 3D magnetic susceptibility tomography of the part or material.

There are many applications for this invention. One would be to mix a nanoparticle signature into the epoxy backing of microchips. This application would provide an integrated nanoparticle signature that would make counterfeiting significantly more difficult. Another application would be to label repairs done with epoxy, plastic or other materials such as concrete. A nanoparticle signature would be added to the material prior to the repair and this signature would correspond to a record of the repair for future inspection and reference. Another application is to label manufactured parts and 3D printed parts with an embedded label for tracking and authentication purposes. Another application is in construction and other applications where accurate mixing ratios are important. Magnetic nanoparticles could be added to the substrates or during the mixing process and later scanned to ensure proper mixing. An additional application is document labeling and authentication. Another application is tracking of tool wear and/or liquid leakage by scanning residues for magnetic nanoparticle content.

Magnetic particles have been used in ink for document authentication and other applications, but not at the size scale of nanoparticles. This is a significant difference because magnetic nanoparticles that are smaller than a single magnetic domain are paramagnetic or superparamagnetic rather than ferromagnetic, which means that the particles do not carry a residual magnetization. This means that the susceptometer must actively probe the susceptibility with an applied field as opposed to reading a residual magnetic field. Paramagnetic and superparamagnetic materials may be exposed to high magnetic fields without damaging the information contained within the part or material. Since the nanoparticles are paramagnetic or superparamagnetic, they do not retain any magnetic field after the susceptometry reader is removed so the nanoparticles will not interfere with sensitive equipment. This feature also makes the nanoparticle signature more covert because it will not trigger metal detectors or magnetometers. In addition, the idea of distributing nanoparticles in a material in a 3D pattern to be later scanned allows for a much higher information density to be imparted into a part or materials than the surface application of ink.

With high enough information density from the proposed nanoparticle method, highly complex digital codes or substantial amounts of digital information can be incorporated. This digital information could include, for example, time and date stamps from manufacturing, product numbers, test and validation data, user manuals, pricing information, and re-ordering information. Information could also be encrypted or non-encrypted. Information could be related to the product that is marked or covert or overt for entirely different purposes such as advertising, data transfer, data storage, and monetary authentication.

The proposed magnetic nanoparticle taggant method and reader device offers an inexpensive method for encoding parts with a signature that will live with the part throughout its lifecycle. This is a method for authentication, tracking, and supply chain management. It is also a method of labeling that can work on difficult products, such as small parts or inexpensive parts. The method also solves labeling of parts in a non-discrete fashion and materials like liquids, cables, tubes and other large parts can contain a distributed single label that ties all parts of the product together.

Properties of Sensors

Magnetic neurological signals can be characterized by both their frequency and their magnetic field strength. In general, brain activity occurs between 0.1 and 1000 Hz and the magnetic field strength from this activity as measured by MEG ranges from 40-2000 femtotesla. In order for a device to measure brain activity without the need for large amounts of signal averaging, the noise either measured by or inherent to the device must be below the field strength of the brain signal at the frequencies of interest. For example, the alpha rhythm occurs between 6-12 Hz and has field strength of roughly 1000 femtotesla. In order to measure this rhythm, a device would ideally have noise much less than 1000 femtotesla between 6-12 Hz. This noise threshold is an extremely difficult barrier for many devices to overcome.

For liquid-helium cooled MEG SQUID sensors, noise is roughly 3.5 femtotesla/$\sqrt{Hz}$, low enough for this type of measurement. High temperature SQUID sensors have noise around 40 femtotesla/$\sqrt{Hz}$, which is low enough to measure most types of brain activity. Commercial MEG machines often use SQUID sensors, a state of the art MEG system can measure fields ranging from 20 nanotesla down to the noise floor of 3.5 femtotesla, corresponding to an inherent range-to-noise ratio of $5.7 \times 10^6$.

Sander has published a report on a chip-scale atomic magnetometer that had a noise floor around 200 femtotesla/$\sqrt{Hz}$ and they describe theoretical work that indicates that a noise floor of 3 femtotesla/$\sqrt{Hz}$ may eventually be achievable (T. H. Sander, J. Preusser, R. Mhaskar, J. Kitching, L. Trahms, and S. Knappe, "Magnetoencephalography with a chip-scale atomic magnetometer." Biomed Opt Express, vol. 3, no. 5, pp. 981-990, May 2012.). With this device they were able to measure brain activity and stated that, because of the sensors' size, the sensors were able to be moved closer to the brain. Since magnetic fields emitted from the brain drop off rapidly with distance, this permits measurement of larger magnetic field strengths from the brain than practical with cryogenically-cooled sensors like SQUIDs. Atomic magnetometers are estimated to have sensitivity ranges from roughly 1000 nanotesla down to the noise floor of 200 femtotesla, corresponding to a range-to-noise ratio of $5.0 \times 10^6$. If an atomic magnetometer can be built that approaches the SQUID noise floor of 3.5 femtotesla, then the range-to-noise ratio would be $3.0 \times 10^8$.

While these sensors have proven to have a noise floor small enough to measure brain activity, another type of sensor that has yet to be able to make MEG measurements is a Fluxgate Magnetometer. The lowest noise floor we have found for a small Fluxgate is around 4000 femtotesla/$\sqrt{Hz}$. Even in the most optimistic case, this type of noise would require experimentation where a large amount of averaging was possible. This could potentially be done in experiments where an input rhythm is tracked by the brain so that noise averaging could make up for the poor noise floor. However, noise averaging inherently means that more data is needed to see the same result and so long tests are necessary.

A fluxgate magnetometer offers a sensor with reasonable bandwidth and a large measurement range-to-noise ratio. Fluxgates can measure magnetic fields from 100 microtesla to their noise floor of 10 picotesla, which amounts to a range-to-noise ratio of $1.0 \times 10^7$. This type of range-to-noise ratio becomes important for magnetic susceptibility tomographic (MST) imaging of blood, see below.

An Embodiment Based on SQUID Sensors

A MEG-MST dual-function system 100 (FIG. 1C) makes use of a magnetically shielded room (MSR) 102 in order to minimize stray magnetic fields that may otherwise impair measurements. Some MSRs employ passive shielding materials such as layers of mumetal and aluminum. Other MSRs also employ active shielding by detecting the magnetic field disturbances and compensating for the detected noise with large coils placed on the walls of the MSR. Nonmagnetic subject-positioning apparatus, such as a wooden chair 106, couch, bed, or recliner, upholstered with foam padding but not springs, is provided on which a subject may sit or recline, and an array of magnetic sensors and bias coils are provided in a hemispherical sensor helmet 108. The helmet has an inner diameter sufficient to surround a measurement volume, the measurement volume large enough to enclose most human heads in vivo, and has magnetic sensors positioned to sense magnetic fields emanating from sources that may be positioned within the measurement volume. In an embodiment having superconducting quantum interference device (SQUID) magnetic sensors, the sensor helmet 108 is thermally insulated to prevent heat from either a subject or from the MSR from reaching the SQUID sensors, and provided with Dewar-reservoir apparatus that bathes the sensors in cryogenic liquids to keep the sensors cold enough to function properly. The sensor helmet is also provided with sensor electronics 110 for using its magnetic sensors to measure magnetic fields, as well as bias coils for providing an alternating-current (AC) magnetic field, and compensation coils for reducing the direct coupling of bias fields to the sensors, which are used together for measuring paramagnetic properties of materials, such as the living biological materials of a human or animal head, including brain, that may be placed within the helmet. The helmet is also provided with a mechanical support and positioning system 112 that permits the helmet to be positioned about a head of a subject when the subject is on the subject-positioning apparatus. In an embodiment, a well-shielded subject-stimulus subsystem 114 for visually and aurally stimulating a subject is also positioned to provide audio and visual stimulus to a subject within the MSR. The compensation coils are coupled to be driven by a plurality of compensation coil drivers, the compensation coil drivers in turn coupled to the processor 124, wherein the processor comprises machine readable instructions for controlling the compensation coils to cancel bias fields at the sensors. Similarly, in an embodiment the bias coils are coupled to be driven by bias coil drivers, the bias coil drivers in turn operating under control of processor 124.

It is anticipated that magnetic susceptibility imaging devices may be constructed with other shapes for imaging other biological materials. In an embodiment, a cup-shaped imaging head 115, having structure similar to an inverted version of that described for the helmet including magnetic sensors, bias coils, and compensation coils, placed below a hole in a platform 113 (FIG. 1D) such that a woman lying on platform 113 may dangle her breast 121 into imaging head 115, which operates with electronics 117 similar to that described herein with reference to SQUID sensor electronics, power conditioning 118, data acquisition 120, coil drivers 126, Since the sensors can pick up stray magnetic fields, and such fields can be emitted by electrical currents in wiring, as much as possible of system electronics is located outside the MSR. Further, any electrical power required by apparatus, such as SQUID-sensor electronics 110 that is positioned within the MSR, is conditioned by power conditioning electronics 118 to reduce fields at frequencies of interest from power-line ripple; power conditioning electronics 118 also provides clean, regulated, power to lock-in amplifiers 119, data acquisition 120, and bias-coil and compensation coil drivers 126. Electronic portions of sensor electronics 110 and stimulus system 114 that are physically located within the MSR are magnetically shielded to reduce interference. A subject-response device 116, such as a pressure-sensitive switch or touchpad, is located where it may be reached by a subject on the subject-positioning apparatus.

Signals from sensor electronics 110 and response device 116, and to stimulus system 114, are preferably transmitted on optical fiber to prevent interference. Signals from sensor electronics 110 are coupled to data acquisition electronics and filtering 120, which provides digitized data to a digital processor and image processor 124 having memory 122. Also operating under control of processor 124 are High-Q AC bias-coil interfaces and coil drivers 126 that are coupled to bias coils of the helmet 108.

Figure 2:
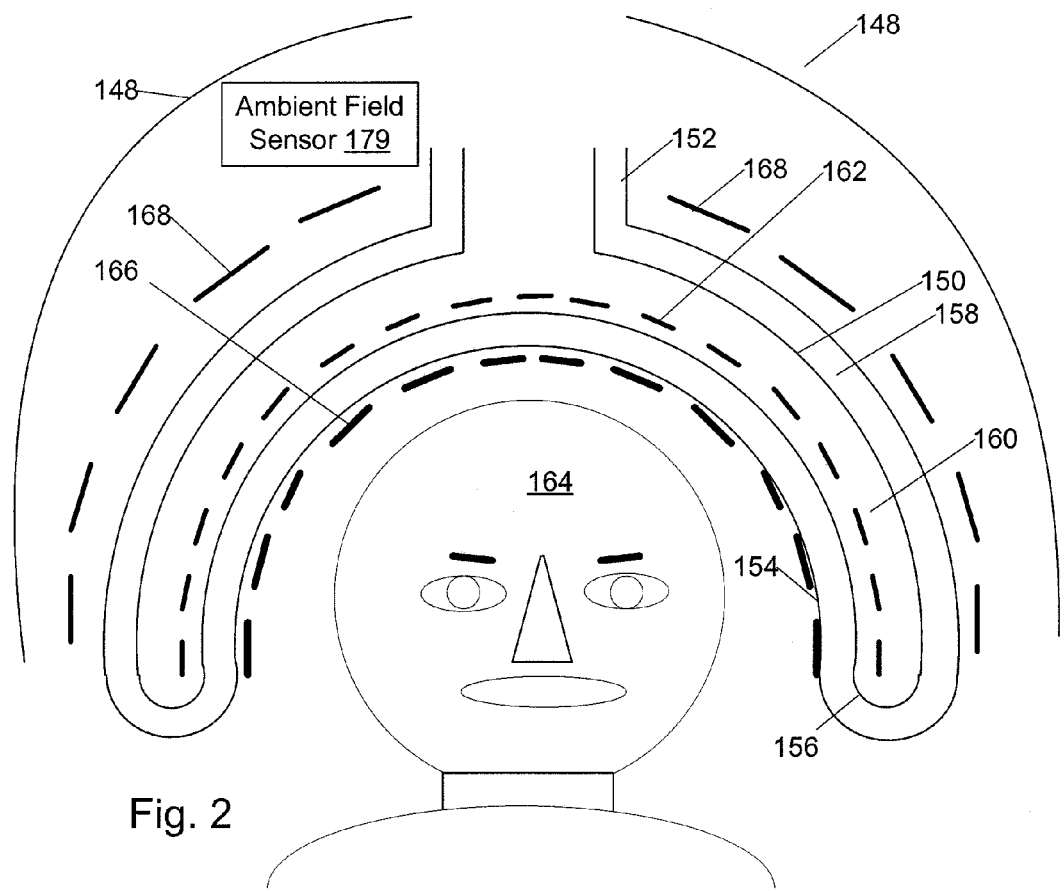
FIG. 2 illustrates schematically in cross section the coils for applying magnetic fields and magnetic field sensors of a sensor helmet of a dual-modality MEG-MST imaging machine.

In an embodiment, helmet 108, or inverted as cup 115, has a magnetic shield 148, as illustrated schematically in FIG. 2. Within shield 148 are inner 150 and outer 152 Dewar walls that define its shape. These walls are bent upwards to form a helmet cavity, also forming inner-inner 154 and inner-outer 156 Dewar walls. A space 158 between inner-inner 154 and inner-outer 156, and between inner 150 and outer 152 walls is evacuated for insulation. A cooled space 160 within the helmet is filled with cryogenic refrigerant and also contains multiple superconducting quantum interference devices (SQUIDs) 162 positioned to detect and measure magnetic fields emanating from, or modulated by, a head 164 of a subject that may be present within the helmet. Also included within the helmet are multiple bias coils 166 for providing a magnetic field to the head 164 of the subject, the bias coils 166 forming a layer between the SQUIDs 162, or other sensors, and head 164 and configured to provide bias magnetic fields for sensing magnetic susceptibility in head 164. Also provided are multiple compensation coils 168 forming a layer distal from head 164 relative to SQUIDs 162 that are used to null the bias magnetic fields at the SQUID sensors. In some embodiments, one or more 3-axis ambient magnetic field sensor 179 is included within a first layer of shielding 148, the ambient magnetic field sensor is configured to measure stray magnetic fields, such as those that may penetrate shielding and originate from sources outside the system and subject such as the Earth's magnetic field, building wiring, passing vehicles, elevator motors, air conditioners, workmen's tools, cellular phones, and other sources. Readings from ambient magnetic field sensor 179 may, in some embodiments, be used to provide compensating fields by adjusting electromagnets within the system, and may be used to provide feedback to control current in ambient-field compensation magnets (not shown) that provide fields determined to cancel ambient magnetic fields.

Figure 2A:
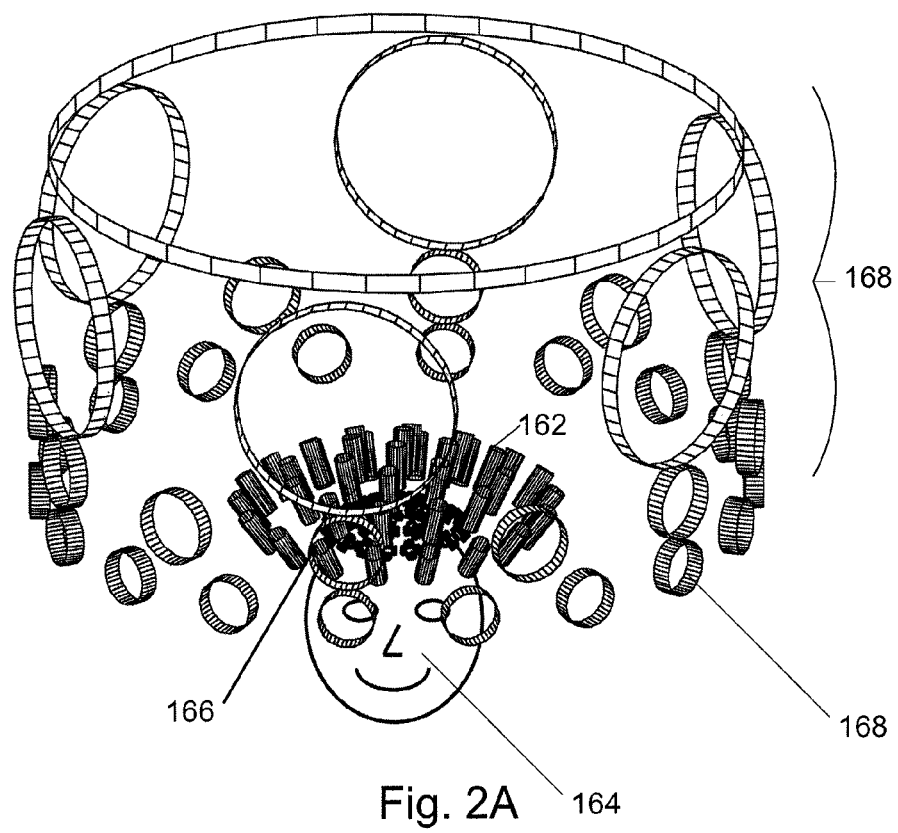
FIG. 2A is a perspective drawing illustrating a configuration of coils and sensors illustrating a configuration of use when building a magnetic susceptibility tomography machine by retrofitting bias and compensation coils to an existing magnetoencephalography machine.
Figure 2B:
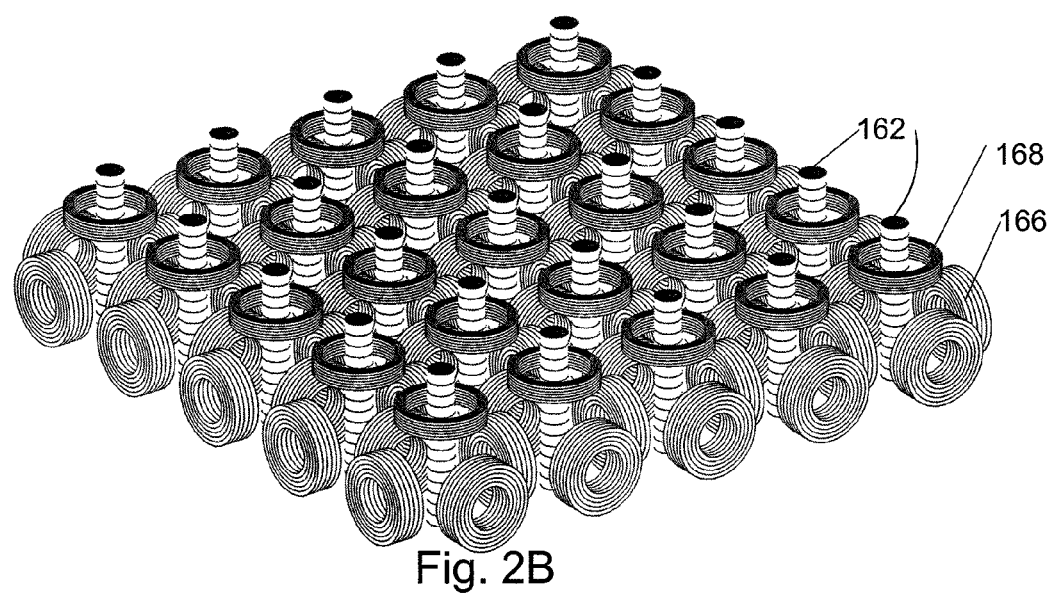
FIG. 2B is a perspective drawing of a configuration of coils and sensors illustrating a configuration with bias and sensor coils in close proximity to sensors.

In some embodiments, such as the embodiment illustrated in FIGS. 2 and 2A, conventional, non-superconducting, electromagnet coils are used for both bias coils 166 and compensation coils 168. In the embodiment of FIG. 2A, intended for retrofitting to a pre-existing SQUID-based magnetoencephalograph, bias coils 166 are placed between Dewar 152, 156 and its layer of sensors 162 and head 164, while compensation coils 168 (illustrated as rings in FIG. 2A) are placed external to Dewar 152, 156 and its layer of sensors 162 (illustrated as rods in FIG. 2A).

Where a magnetic susceptibility tomography machine is initially built for that purpose, the bias coils 166 and compensation coils 168 may be in closer proximity to sensors, as illustrated in FIG. 2B.

It is anticipated that the magnetic susceptibility tomography images may require registration with anatomical images, such as from MRI, or with other functional images such as from fNIRS (functional Near-Infrared Spectroscopy neuroimaging). Fiducial markers may be used to facilitate this registration by providing a frame of reference that can be located in both imaging systems. Suitable fiducial markers for magnetic susceptibility tomography should have at least one portion with sufficiently different magnetic susceptibility from water and air to provide good image contrast and should be small enough in size to accurately model as magnetic dipoles. In some applications it may be desirable to use a calibrated standard for a fiducial. For these applications, the National Institute of Standards and Technology (NIST) SRM 764a magnetic susceptibility standard 2 mm×3.42 mm platinum cylinder may be used. Alternatives are the NIST 762 Magnetic Moment Standard Nickel Disk, and the 772a Nickel Sphere for Magnetic Moment. In other applications where the fiducial need only provide a reference mark, other materials such as iron or iron oxide are used. Additional bias coils may be placed on anatomical landmarks and used as active fiducial markers. The signals from the active fiducial markers are generated by supplying AC currents to the active fiducial markers at specified frequencies that are reserved for this purpose. The signals from the active fiducial markers may be extracted from the sensitive magnetic sensor readouts using lock-in amplifiers.

It is often desirable to have a fiducial that is visible in more than one imaging modality, such that it may be used directly to register images as an alternative to relating a fiducial location to a known point of anatomy and finding anatomy in images. Some of these markers, such as platinum cylinders and nickel disks, are also visible in other modalities such as CT. If the same markers are to be used in alternative imaging techniques, the markers may have one portion that is visible in MST and a second portion visible in a specific alternative imaging methodology. In an example fiducial, the fiducial has iron oxide embedded in a plastic to provide contrast for MST, the plastic enclosing an air bubble to provide contrast in ultrasound imaging. In a second example fiducial, a fiducial both has magnetic particles or nanoparticles and high density so as to be visible in X-ray and CT images, such as iron oxide particles suspended in a lead casting, the lead casting in turn covered with a biocompatible material and is visible in MST, CT, and MRI. In a third example fiducial, a fiducial both has a plastic pedestal that can accept a capsule of iron oxide particles to provide contrast for MST or a capsule of vitamin E to provide contrast for MRI. The capsules may be exchanged in the plastic pedestal without removing the pedestal so that the collocation of the fiducial markers in the MST and MRI images is preserved. Fiducial markers may be adhered to anatomical landmarks with tape or biocompatible glue or implanted. The magnetic susceptibility tomography images can then be rigidly or non-rigidly transformed until registered with the anatomical or functional images from another system.

Lock-In Amplifier

Figure 5:
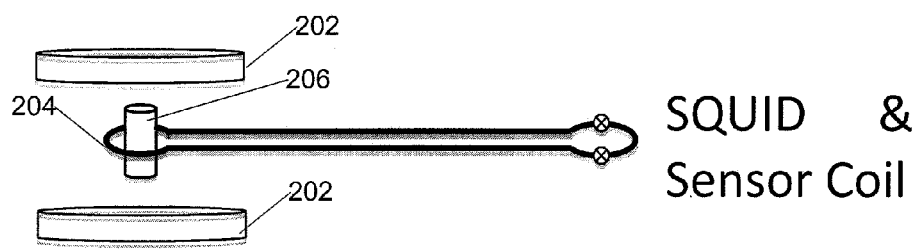
FIG. 5 illustrates the principle of determining magnetic susceptibility by applying a magnetic field, and measuring magnetic field at a sample location both with and without a sample present.
Figure 5A:
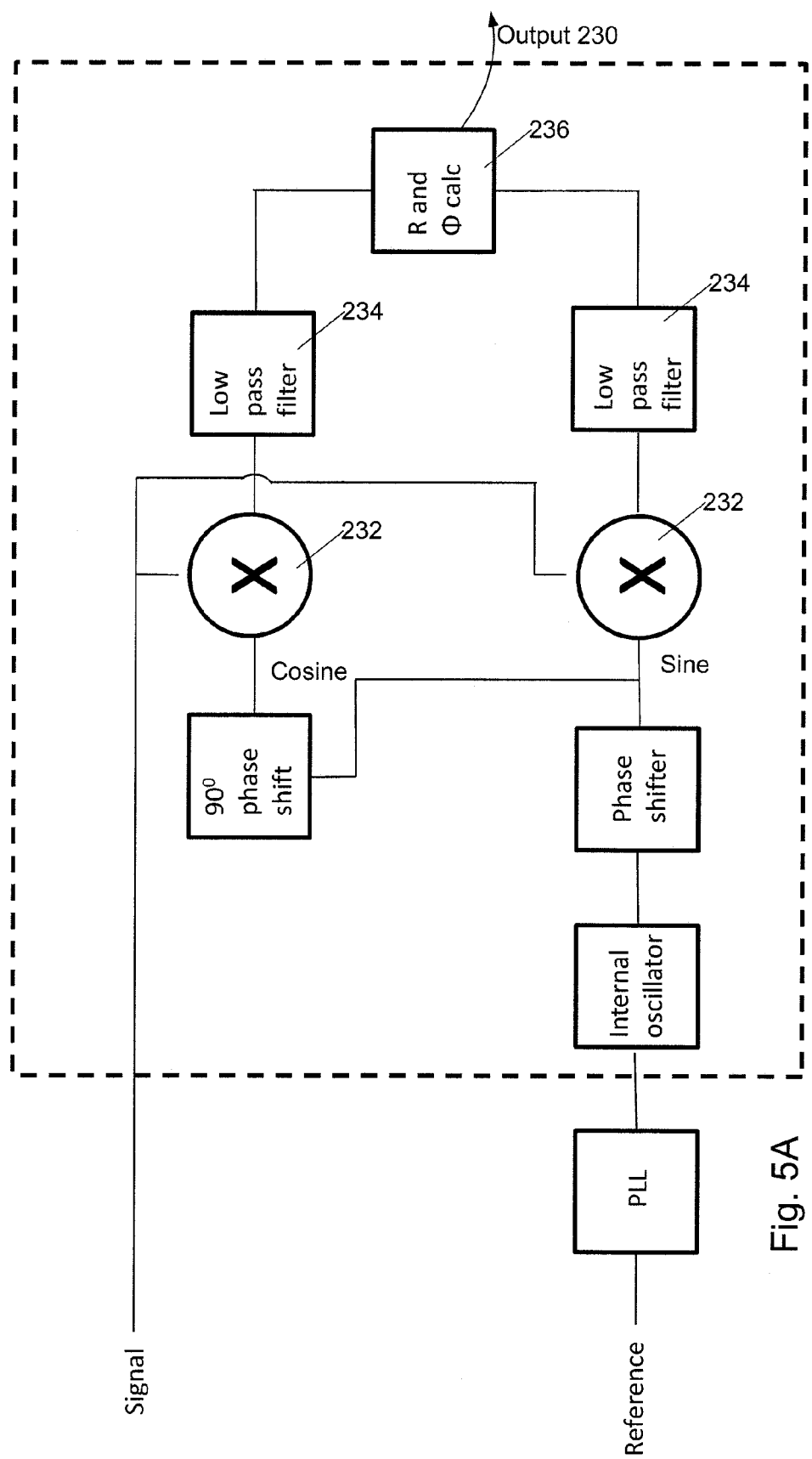
FIG. 5A illustrates a lock-in amplifier of use for separating signals from noise prior to image reconstruction, the signals received from a sensor.

A lock-in amplifier is an analog or digital device used for noise reduction when an oscillatory signal of known frequency and phase is being measured, and is illustrated in FIG. 5A. The lock-in amplifier may also be implemented in software routines in computer processor. To work effectively, a REFERENCE signal of the same frequency as the oscillatory signal and a known phase is provided to the lock-in amplifier along with the signal of interest SIGNAL. A lock-in amplifier measures the frequency and phase of the reference signal and creates a sine and a cosine waveform. These reference waveforms are multiplied with the signal of interest in multipliers 232. This multiplication will result in a new wavefoini with several components. If the signal of interest contains a waveform at the same frequency and having a constant phase with respect to the reference, then this new waveform will have an amplitude component proportional to this oscillatory component in the signal of interest. Other frequency components will be shifted in frequency space and random components like thermal noise will be reduced through averaging due to their non-constant phase. Next, the amplitude is extracted by low pass filtering the new waveform in filters 234. Finally, the amplitude and phase of the signal are determined in Amplitude and Phase conversion block 236, and the amplitude and phase outputs are provided in digital form as measures of the magnetic field for MEG or MST reconstruction by processor 124. This process is very effective at high sampling rates since noise is cancelled as a function of the square root of the sampling rate reduction from input to output. An analog device is able to achieve noise reduction of up to 60 dB, while a digital device is able to reduce noise up to 120 dB.

Magnetic Field Compensation

Typically the dynamic range limit of a magnetic field sensor and/or analog to digital converter (ADC) and/or digital to analog converter (DAC) prevent a continuous wave (CW) AC susceptometry system from being able to achieve high levels of sensitivity. In an embodiment, we overcome this limitation by using one or more compensation coils 168 in combination with high precision ADCs and DACs to reduce the directly coupled signal from the bias coils 166 or excitation field to sensors 162 so that the available dynamic range can be applied fully to the signal of interest. The CW method using unique excitation frequencies combined with multiple compensation coils enables many measurements to be obtained simultaneously from the target region for tomographic image reconstruction. One of the advantages of using compensation coils is that the dynamic range of the analog-to-digital conversion (ADC) does not include the applied field because the net field at the sensor is a vector sum of the compensation field and bias fields, and compensation fields are chosen to reduce net field at the sensors. Without the compensation coils the acquisition range for the ADC needs to encompass the directly coupled bias field making bit noise larger than the signal of interest from the sampled medium. The compensation coil approach solves this problem by reducing the direct coupling of the bias field into the sensors. Spatial distortion of the bias field in the medium being imaged can be accounted for in the tomographic imaging algorithm without any loss of resolution or sensitivity.

Several approaches can be taken to build the compensation circuitry. The most flexible is to use a DAC with enough dynamic range to produce a magnetic field capable of eliminating the bias field at the sensor while not increasing the noise measured at by sensor. In the case of a single bias field, the bias field and the compensation field can have the same signal to noise ratio (SNR), but when multiple bias fields are in use, the compensation field must be able to eliminate each bias field individually and thus must have a larger SNR than each bias field. It is possible to solve a system of equations to determine the compensation field strength for a system with many compensation and bias coils. A DAC has the ability to dynamically change the applied field to accommodate a calculated compensation level that is much harder to achieve with an analog system. Another method that can be employed to compensate a bias field is to use a combined analog and digital system. In this situation, the analog system produces a compensation field close to the bias field strength. The digital system is be used to tune the field in order to achieve optimal compensation. In this way, a high SNR analog signal could be produced in addition to a lower SNR digital signal and still achieve a high degree of compensation. Another compensation scheme is to precisely tune the bias and compensation fields during manufacturing and then use high precision manufacturing to create a fully analog compensation system, with no digital components.

Magnetic Encephalography

While magnetoencephalography directly measures magnetic fields associated with neural activity, magnetic susceptibility tomography measures tissue composition, and tracks changes to tissue composition. Changes in oxygenation of hemoglobin, for example, cause changes in magnetic susceptibility of blood that are detectable with the apparatus described herein.

Magnetoencephalography alone can be performed with the apparatus of FIGS. 1 and 2 by ceasing drive to bias coils 166 and measuring magnetic fields emitted from a brain in a head located within the measurement volume using sensitive magnetic sensors such as SQUID sensors 162. The measured fields may then be mapped to produce tomographic images by processor 124 executing magnetoencephalographic tomography routines from memory 122. The magnetoencephalographic tomography routines include machine readable instructions for directing processor 124 to divide the measurement volume into voxels, to determine field strengths of magnetic fields emitted from each voxel, and construct tomographic images displaying those field strengths as images.

Simultaneous magnetoencephalographic tomography and magnetic susceptibility tomography is described below.

A SQUID magnetometer measures the magnetic flux density B in the direction u normal to the sensor coil $$B_{mag} = B \cdot u$$ Eqn. 1.

A SQUID gradiometer readout measures the difference in magnetic flux density B between its upper and lower coils in the direction of a unit vector u normal to the SQUID coils and relative to the separation of the coils d $$B_{grad} = \frac{B_{lower} \cdot u_{lower} - B_{upper} \cdot u_{upper}}{d}.$$ Eqn. 2

In general the magnetic flux density B at position r from this arrangement contains a magnetic field strength H from free current I in the current loop and a magnetization field M from the magnetically susceptible material $$B(r) = \mu_0 [H_{coil}(r) + M_{tissue}(r)]$$ Eqn. 3.

where $\mu_0$ is the magnetic constant or the magnetic permeability in a vacuum. Below saturation, the magnetization field strength M in the sample at position s is linearly dependent on the volume magnetic susceptibility $\chi_v$ of material in the voxel and the magnetic field strength $$M_{tissue}(s) = \chi_v H_{coil}(s)$$ Eqn. 4.

Magnetic Susceptibility

Magnetic susceptibility is a material property that describes the magnetic response of a material to an applied magnetic field. The magnetic susceptibility response occurs through the alignment or anti-alignment of magnetic domains in the material. Several types of magnetically susceptible materials exist. The magnetic domains of paramagnetic materials will align with an applied field, while the domains of diamagnetic materials will align against the field. Materials with a persistent magnetic field after being magnetized by an applied field are called ferromagnetic. Where ferromagnetic materials are in particle form having sizes less than approximately 50 nm, the size for single magnetic domains, the particles become superparamagnetic.

In the superparamagnetic state and in the absence of a magnetic field, the average magnetization of nanoparticles will sum to zero if measured over a long time window. However, the magnetic moment of a nanoparticle will have two stable orientations separated by an energy barrier. There exists a probability of flipping between orientations that is described by a time constant known as Neel Relaxation. These superparamagnetic nanoparticles also have very high magnetic susceptibility. Iron-core nanoparticles are paramagnetic or superparamagnetic depending on the particle size.

Figures 3, 4:
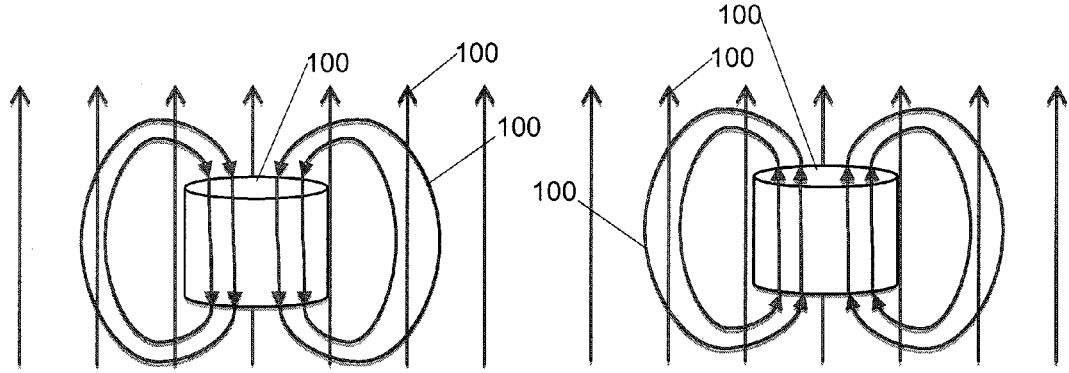
FIG. 3 illustrates lines of magnetic force developed by a diamagnetic, magnetically susceptible, material when exposed to a magnetic field.
FIG. 4 illustrates lines of magnetic force developed by a paramagnetic, magnetically susceptible, material when exposed to a magnetic field.

Magnetically susceptible materials may be paramagnetic (FIG. 4) or diamagnetic (FIG. 3). Diamagnetic materials are defined as having $\chi_v < 0$ and paramagnetic as having $\chi_v > 0$.

The relationship between magnetic flux density B and magnetic field strength H and magnetic susceptibility $\chi_v$ is $$B = \mu_0 (1 + \chi_v) H$$ Eqn. 5

The magnetization M of a susceptible material is proportional to the strength of an applied magnetic field H. $M = \chi_v H$ where $\chi_v$ is the volume susceptibility of the material. In an AC measurement, $\chi_v$ is expressed as $\chi_v = \chi_v' - i \chi_v''$ where $\chi_v'$ is the real or in phase component and $\chi_v''$ is the imaginary or quadrature component of the susceptibility. This magnetization will result in an altered magnetic field B, as measured from a sensor location.

In an embodiment, the applied magnetic field H is created by driving electric current though a coil. The magnetic field strength produced by a coil is directly proportional to the input current. For a point outside of the loop but on the primary axis, the field strength is, $$H = \frac{1}{4\pi} \frac{2\pi R^2 I}{(z^2 + R^2)^{3/2}}$$ Eqn. 6 where R is the coil radius, I is the current and z is the distance from the center of the coil. This is convenient because the current can be produced by an accurately controlled source and the magnetic field can therefore be found by using an accurate model of the coil used to produce the field.

A magnetic dipole has a field strength H that is expressed as $$H = \frac{1}{4\pi}\left(\frac{3r(m \cdot r)}{r^5} - \frac{m}{r^3}\right) \quad \text{Eqn. 7}$$

where r is the radial distance from the source. This field drop off will limit detection as noise becomes more significant farther from the source.

In an embodiment, the applied magnetic field H from bias coils 162 is modified by driving electric current though a compensation coil 168 that is differently positioned from the applied field or bias coil 162 such that the combination of the applied field and compensation field results in a reduction of the total field at the sensor location.

Magnetically Susceptible Biological Materials

Most biological molecules in the human body are diamagnetic, which is defined as any material with $\chi_v < 0$ and is shown in FIG. 3. This means that biological tissue has the effect of reducing the magnetic field. Reduced hemoglobin (HbR) is often referred to as being paramagnetic, which is usually defined as any material with $\chi_v > 0$ and is shown in FIG. 4; however HbR is more precisely termed less diamagnetic than surrounding tissues. Table 1 lists some representative biological susceptibility values. Under the assumption that the change in magnetic susceptibility of HbR is determined by the oxygenation state of the hemoglobin bound iron, the magnetic susceptibility of a partially oxygenated red blood cell (RBC) is simply the linear interpolation between the oxygenated and deoxygenated RBC values given below as determined by the RBC's percent oxygenation.

TABLE 1

Magnetic susceptibility values (SI Units)

| Deionized Water | Deoxygenated Red Blood Cell | Ferritin | Oxygenated Red Blood Cell | Iron (II) Chloride |
|---|---|---|---|---|
| $-9.03 \times 10^6$ | $-8.77 \times 10^6$ | $239 \times 10^6$ | $-9.05 \times 10^{-6}$ | $4,620 \times 10^{-6}$ |

Since brain tissue is not entirely blood cell, it is expected that change due to function will be substantially less than these numbers, resolution of $10^{-7}$ to $10^{-8}$ would be desirable.

Locating Iron-core Nanoparticles

The magnetic susceptibility of nanoparticles can be much greater than biological tissues. For example, consider 110 nm $Fe_3O_4$ iron core nanoparticles from Micromod Gmb (Rostock, Germany). In a particular suspension these nanoparticles are concentrated at 8.13 mg Fe/g and have a very high susceptibility of $6.5 \times 10^{-4}$ m³/kg as compared to water, which has a susceptibility of $-9.05 \times 10^9$ m³/kg. The difference in susceptibility between these particles and water provides the contrast that is measured in nanoparticle contrast imaging. It is important to note that in biological studies these nanoparticles are highly diluted and therefore the effective susceptibility of a biological sample is much closer to that of water. For instance, the concentration of nanoparticles might be diluted as much as a factor of 100 from the above. Typical concentrations range from 0.1 mg Fe/ml to 0.5 mg Fe/ml but may be much higher or lower in some applications.

Since the effect of concentrations of these iron-core nanoparticles in tissue is to alter magnetic susceptibility of the tissue, these nanoparticle concentrations can be located by magnetic susceptibility tomography as herein described, and as performable with embodiments based on all three sensor types, SQUID, fluxgate, and atomic magnetometer. Since high concentrations of nanoparticles can significantly alter magnetic susceptibility, high concentrations of nanoparticles can be readily located even with equipment insufficiently sensitive to perform MST on unlabeled biological tissues.

Bulk Magnetic Susceptibility

Bulk magnetic susceptibility is the average physical property of a sample that describes the induced magnetic field produced by the matter when in the presence of an applied magnetic field.

A prior method to quantify susceptibility $\chi_v$ places a cuvette filled with the sample to be characterized in presence of a SQUID or other magnetic sensor and an applied magnetic field, the applied magnetic field here provided by solenoid coils 202 (see FIG. 5). The sensor 204 is placed within the applied field, and field is measured. A sample 206 is then placed within the field, and the field at the sample location is re-measured. The difference in the magnetic field measured with the sample present versus with the sample absent is a direct measure of the induced magnetic field and is used to calculate $\chi_v$.

The measurement of bulk magnetic susceptibility has been used with three dimensional objects when an average value for a single body in space is desired. The applications of this technique in humans have included temporal characterization of the cardiac cycle and iron stores in the liver and spleen.

We are unaware of prior study of magnetic susceptibility in vivo in human or animal brains, or of prior magnetic susceptibility tomography of human or animal brains.

Anticipated Signal Strength

Imaging hemodynamics with intrinsic magnetic susceptometry contrast is based on detecting small changes in the magnitude of the measured B-field from local changes in the volume of deoxyhemoglobin (HbR). The contrast from a sample of fully deoxygenated blood in water arises from the difference between $\chi_v$ for deoxygenated red blood cells ($-8.77 \times 10^{-6}$) and water ($-9.03 \times 10^{-6}$), which results in $\Delta\chi_v = 2.6 \times 10^{-7}$. The susceptibility of oxyhemoglobin (HbO) ($-9.05 \times 10^{-6}$) is very close to water. It is also necessary to account for hematocrit, which indicates the blood volume fraction comprised of hemoglobin (~40%) and the blood volume fraction in the grey matter of the brain (5%). This means that the maximum local field contrast from intrinsic susceptometry is $5.2 \times 10^{-9}$ times the applied field. Considering that it is desirable to detect functional responses of the brain from oxygenation changes on the order of a few percent and that the signal of interest is further reduced due to the distance between the brain and the SQUID coils, the induced field contrast is 10 billion times smaller than the applied field. This corresponds to a minimum dynamic range dynamic requirement of 200 dB. Modern SQUID-based MEG systems can measure between ±20 nanotesla to a smallest bit of 2 femtotesla, which is a dynamic range 140 dB. This means that prior MEG systems are 60 dB or 1000 times short of the necessary capability to make the susceptometry measurements. An applied field of 20 nanotesla would result in a susceptibility response from the brain on the order of 2 attotesla.

When enclosed in a high-quality magnetically shielded room, the noise from a SQUID system is dominated by the thermal noise of the SQUIDS. The thermal noise floor of a SQUID system is 3.5 fT/√Hz above 1 Hz. Hemodynamics has slow physiological dynamics relative to neural activity. Most studies of neural dynamics with EEG and MEG use sampling rates of up to 500-1000 Hz whereas hemodynamics measured with NIRS (which is not rate limited like fMRI) uses sampling rates on the order of 10-50 Hz. The thermal noise from SQUIDs for hemodynamics is therefore also 1000 times larger than the susceptometry signal from a 20 nanotesla applied field. Overcoming this dynamic range gap and poor signal to noise ratio is essential to the present device.

Prior SQUID susceptometry overcomes the challenge of measuring blood by using uniform applied fields on the order 1 millitesla or even 1 T and gradiometers rather than magnetometers near the sample so that a susceptibility response on the order of 1 nanotesla can be measured. However, this approach of using a strong applied field creates too much noise in the SQUIDs to simultaneously make MEG recordings of intrinsic biomagnetic fields from neural activity that is on the order of femtotesla to picotesla.

Our approach is to keep the applied field seen by the SQUID sensors 162 within the ±20 nanotesla range that permits low noise SQUID operation for MEG measurements while using additional instrumentation and methods to achieve sensitivity to the attotesla susceptometry signals. The increase in dynamic range and reduction of noise are accomplished by a combination of methods: We use alternating current (AC) in the coils to generate the applied field. The components of the applied field from bias coils 166 that are directly coupled to the SQUIDs 162 are attenuated by mean of compensation coils 168. The geometric configuration of applied field and compensation coils exploit orthogonal arrangements, positional offsets, and size scales so that the compensation fields minimally attenuate the applied fields in the imaging region. This compensation scheme permits a much stronger applied field to be used than the ±20 nanotesla range that permits low noise SQUID operation. The limit on the amount of increased applied field strength permitted by compensation is the noise introduced in the SQUID measurements at MEG frequencies of interest from the applied field and compensation coils rather than the amplitude of the applied field at the AC carrier frequencies. Available MEG systems have sampling rates of up to 5 kHz so the available frequency range is up to the Nyquist frequency of 2.5 kHz. Suppose a frequency of 1 kHz is used. By using a high Q-factor oscillator, the bandwidth of the oscillation frequency can be exceedingly narrow, such as within $20 \times 10^{-6}$ of the oscillator frequency. Since any frequency instability in the high Q-factor oscillator is coupled into the susceptometry signal of interest that is measured by the SQUID sensors, a lock-in amplifier 119 is used to greatly reduce the noise in the desired amplitude measurement prior to analog-digital conversion in data-acquisition and filtering unit 120. The needed reference signal is obtained by precisely measuring the current in the oscillator coil. Currently available lock-in amplifiers using a quality reference signal can reduce noise levels by 60-120 dB. The noise reduction from the lock-in amplifier is proportional to the square root of the bandwidth of its bandpass filter centered on the modulation frequency. SQUID sensors have an inherent bandwidth on the order of $1 \times 10^9$ Hz and SQUID MEG systems are sometimes configured to have sample rates of $1 \times 10^6$ Hz to $1 \times 10^8$ Hz. This high sample rate of SQUID MEG systems means that the bandpass filter in a lock-in amplifier can have an exceedingly narrow bandwidth even for a short data record. The signal-to-noise improvement achievable with the lock-in amplifier is enough to overcome the 60 dB deficit and measure susceptometry signals from the brain with a signal-to-noise ratio that is much greater than one. When used with a SQUID system with a high sampling rate, the resulting bandwidth of the hemodynamic estimate can be on the order of 10 Hz or more. Further reduction of noise is possible by using multiple AC bias coils, each of which will result in an independent measured signal in the magnetic sensor. The bias coil geometry may also be designed such that the applied field at the sensor location is minimized while maintaining a strong field at the tissue. This can be done for example, by using a spatially uniform applied field with SQUID gradiometers. The uniform field will not excite the SQUID sensors but the local magnetization of the susceptible material will result in a measurable magnetization field.

An alternative approach to the lock-in amplifier is to use digital signal processing (DSP) to track changes in the oscillator frequency and then to use linear regression to fit the amplitude of the oscillator signal in the SQUID over short time window (e.g. 500 samples or 0.1 s). There is a cost advantage to the DSP approach because less hardware is required. When digitizing with an analog-to-digital converter (ADC), it is advantageous to use a system with a high number of digitization bits such as 32-bits to obtain the needed 200 dB signal-to-noise ratio. There are additional methods for ADC error compensation including methods for reducing quantization error. The applied AC magnetic fields from the bias coils act effectively as sinusoidal dithering signals. By averaging over a finite time window and imparting a dither signal that spans a wide bit range, the effective number of bits is increased by 10 or more. The trade-off for this extra precision is a slower sampling rate for the hemodynamics than the neural dynamics but this this can be done while still maintaining an order of magnitude speed advantage over fMRI.

Embodiments Having Fluxgate Sensors

In an embodiment having a fluxgate magnetic sensor, no magnetically shielded room is required, no Dewar-reservoir apparatus is required, because no cooling with cryogenic fluid is required. The bias coils 166 and compensation coils 168 for the fluxgate embodiment may be placed around or beside the fluxgate sensors in any desired configuration. Configurations that provide multiple angles of applied field to the region of interest are desirable.

For fluxgate imaging of magnetic nanoparticles, the applied field strength can be much greater than for a SQUID-MEG system. The sensing range of fluxgate systems varies by manufacturer. For example the FVM 400 (MEDA, Inc., Dulles, Va.) is a vector magnetometer that can measure magnetic fields in the range of ±100 microtesla with ±1 nanotesla noise. The Mag-03 three-axis magnetic field sensors (Bartington Instruments Limited, Oxford, England) has a range capability of up to ±1 millitesla and a low noise sensor capability of ±6 picotesla noise, which is close to 180 dB of signal-to-noise. The signals from nearby fluxgate magnetometer sensors that share a common axis may be differenced to obtain a magnetic field gradient along the common axis. A wide dynamic range fluxgate with time averaging enables measurement or imaging of intrinsic contrast from hemodynamics like the SQUID system except without the MSR and cryogenic cooling. A disadvantage of using a fluxgate for measurement of hemodynamics is that fluxgate sensors lack the ultra low field measurement capability that is needed for simultaneous MEG measurement.

Magnetic Susceptibility Tomography (MST)

MST is a noninvasive method of imaging the distribution of the physical property of magnetic susceptibility through a part of the body or non-biological material, and functional magnetic susceptibility tomography (fMST) is a noninvasive method of imaging changes in the distribution of magnetic susceptibility due to changes in brain function or any reason for time variation in the magnetic susceptibility property of the material being imaged. Both MST and fMST require an applied magnetic field to the material so that the material under examination will produce an induced magnetic field. The induced magnetic fields are then measured, with fMST requiring rapidly repeated measurements. In an embodiment, the apparatus herein described measures magnetic fields with an effective sample rate of greater than or equal to ten hertz, significantly faster than the half-hertz achievable with functional magnetic resonance imaging.

In practice, the spatial reconstruction of volume magnetic susceptibility, $\chi_v$, through the use of magnetometers has been successful in one and two dimensional systems.

One dimensional methods use a presumed shape, often a sphere, for an object of interest. Within the presumed shape, an average susceptibility is solved for by assuming that the object's $\chi_v$, is uniform. Finally, a linear equation relating the $\chi_v$, of the object of interest, the applied magnetic field, B, and the magnetometer location and orientation is created and solved. One-dimensional methods do not provide an image.

Similarly, the two dimensional methods assume a sample of uniform thickness. Since a two-dimensional reconstruction is used the $\chi_v$, is assumed to be uniform in the direction of thickness. The measurements are typically performed by moving a sample through a uniform field with fixed sensor locations; alternative measurements may be made by moving sensors past a fixed sample. The resulting measurement is a convolution of the applied field with induced fields generated in the sample. The measurements are then deconvolved using Green's function to produce resolutions better than 1 mm by accounting for the spatial correlation of the magnetic fields.

To date, three dimensional methods of MST have not been implemented, but the analytical groundwork for one method has been developed. The first step of this method is the voxelation of a computer model of sample space in memory 122 of processor 124 by dividing a measurement volume within the helmet into multiple voxels. Following the voxelation of the sample space, the induced dipole relation is computed for the centroid of each voxel. While this method is applicable for non-uniform fields, this method has only been analyzed for uniform fields thus far; although Sepulveda et al. do recognize that non-uniform fields could be beneficial to the reconstruction (N. G. Sepulveda, I. M. Thomas, and J. P. Wikswo, "Magnetic susceptibility tomography for three-dimensional imaging of diamagnetic and paramagnetic objects," *IEEE Trans. Magn.*, vol. 30, no. 6, pp. 5062-5069, 1994.). The contribution of each dipole is then calculated for each sensor-dipole pair. The number of the sensor dipole pairs in this method is set high enough so as to guarantee an over defined systems. This fundamentally sets the ratio of the number of voxels to number of measurements. The system is then solved in three dimensions by using singular value decomposition. The prior literature on MST is either limited in the dimensions that can be reconstructed or the number of measurements required for reasonable spatial resolutions on size scales of clinical interest.

Of the existing MST techniques, the two dimensional methods have typically used specialized small scale SQUID magnetometer arrangements often with a single sensor coil with a surrounding Helmholtz coil to provide a uniform field in the imaging space. The sample is then moved through the imaging space while the remainder of the apparatus remains fixed.

The one dimensional methods have used two principle approaches. The first is more common in geological investigations where a magnetometer or an array of magnetometers is swept over an area. The location of the sensor(s) is then matched to the sensor readings to achieve estimates of the average underlying $\chi_v$. The other method relies on an advanced assumption of the underlying shape of interest and is often used in clinical imaging to estimate hepatic or splenic iron content. Typically, this method uses magnetometers to measure fields in the presence of an applied field with a spherical shape assumed for the organ of interest and the subject is slowly moved into and/or out of the sensor sensitivity region during data acquisition.

The MST method introduced in the present work reconstructs for a three dimensional volume and does not require an over-defined system, thus, lowering the number of required measurements.

Forward Model

A forward model operable on the processor 124 models the sensitivity of the system's magnetic sensors to variations in magnetic susceptibility throughout the imaging volume, and impact of each. The forward model was generated by breaking the imaging volume into rectilinear elements, referred to as voxels. The applied magnetic field strength was determined for the centroid of each magnetic sensor. This applied field was then used in combination with modeled spatially varying magnetic susceptibility to calculate the strength of the induced magnetic field at each voxel. This induced magnetic field was then projected for all voxels onto the sensor locations.

Computing the Applied Field from the Excitation Coils

The magnetic field strength form the free current can be computed by integrating the Biot-Savart law around the circular loop, which approximates wire as an infinitely thin conductor. The resulting field has a closed form solution (Smythe, W R 1967, *Static and dynamic electricity*, 3rd ed, McGraw-Hill, New York, p. 623). A circular loop in the xy plane carrying current I will generate the magnetic field strength $H_0$ at the center of the loop in the z direction $$H_0 = \frac{I}{2a}, \qquad \text{Eqn. 8.}$$

where a is the radius of the current loop. The magnetic field strength along the z-axis is $$H_z = H_0 \frac{a^3}{(a^2+z^2)^{\frac{3}{2}}}. \qquad \text{Eqn. 9}$$

The off-axis field is given by $$H_z = H_0 \frac{a}{\pi\sqrt{(a+r)^2+z^2}} \left[ E(m) \frac{a^2-r^2-z^2}{(a-r)^2+z^2} + K(m) \right], \qquad \text{Eqn. 10.}$$

$$H_r = H_0 \frac{za}{r\pi\sqrt{(a+r)^2+z^2}} \left[ E(m) \frac{a^2+r^2+z^2}{(a-r)^2+z^2} - K(m) \right], \qquad \text{Eqn. 11.}$$

$$H_\theta = 0. \qquad \text{Eqn. 12.}$$

where the terms K(m) and E(m) are the complete elliptic integrals of the first and second kind respectively and the parameter is $$m = \frac{4ra}{(a+r)^2+z^2}. \qquad \text{Eqn. 13.}$$

The x and y components of the field are computed from the Cartesian components of the radial field $$H_x = H_r \cos(\theta) \qquad \text{Eqn. 14.}$$

$$H_y = H_r \sin(\theta) \qquad \text{Eqn. 15.}$$

where θ is obtained from the four-quadrant inverse tangent function $$\theta = a\tan2(y, x) \qquad \text{Eqn. 16.}$$

Defining the magnetic field strength from a coil at arbitrary position and orientation requires additional transformation steps. Suppose the coil is centered on a point in Cartesian space $(x_{coil}, y_{coil}, z_{coil})$ where the coil is oriented normal to the unit vector $u_{coil} = [u_{coil,x}\ u_{coil,y}\ u_{coil,z}]$, and the objective is to compute the magnetic flux density from the coil at position $(x,y,z)$. The first step is to define the rotation matrix $$R = \begin{bmatrix} \cos(\theta_2) & \sin(\theta_1)\sin(\theta_2) & \cos(\theta_1)\sin(\theta_2) \\ 0 & \cos(\theta_1) & -\sin(\theta_1) \\ -\sin(\theta_2) & \sin(\theta_1)\cos(\theta_2) & \cos(\theta_1)\cos(\theta_2) \end{bmatrix} \qquad \text{Eqn. 17.}$$

$$\theta_1 = a\tan2(u_{coil,y}, u_{coil,z}) \qquad \text{Eqn. 18.}$$

$$\theta_2 = a\tan2\left(-u_{coil,x}, \sqrt{u_{coil,y}^2 + u_{coil,z}^2}\right) \qquad \text{Eqn. 19.}$$

where $\theta_1$ and $\theta_2$ have been derived from the Euler angles between the coil normal and the z-axis. The position $(x,y,z)$ is then translated and rotated relative to the standard frame of the coil defined above.

$$\begin{bmatrix} x' \\ y' \\ z' \end{bmatrix} = R \begin{bmatrix} x - x_{coil} \\ y - y_{coil} \\ z - z_{coil} \end{bmatrix}. \qquad \text{Eqn. 20}$$

Evaluating the field equations at $(x',y',z')$ yields the magnetic flux density in the transformed frame $(H_{x'}, H_{y'}, H_{z'})$. The solution at the desired position requires the application of a final inverse rotation to the magnetic flux density components $$\begin{bmatrix} H_x \\ H_y \\ H_z \end{bmatrix} = R^{-1} \begin{bmatrix} H_{x'} \\ H_{y'} \\ H_{z'} \end{bmatrix}. \qquad \text{Eqn. 21.}$$

If the coil geometry is not well approximated by a single current loop but instead has the shape of a cylinder or annulus then the geometry and total current I can be discretized and summed to obtain a numerical integral approximation to the more complex coil.

The magnetic field $H_{coil} = [H_x\ H_y\ H_z]^T$ from eqn. 21 can be now evaluated in the material sample in the imaging volume $H_{coil}(s)$ in eqn. 4 for computations of the magnetization field $M_{tissue}(s)$, and can be evaluated at the location of the SQUID coils $H_{coil}(r)$ for its contribution to the magnetic flux density $B(r)$ in Eqn 3. The magnetization field contribution to the magnetic flux density at the SQUID coils $M_{tissue}(r)$ will be derived in a later section.

Computing the Compensation Field for Multiple Excitation Coils and Sensors

The magnetic field $H_{coil} = [H_x\ H_y\ H_z]^T$ from eqn. 21 can also be evaluated for each of the excitation coils at the location of the magnetic sensors. This direct coupling of the applied field to the sensors can pose practical problems if it exceeds the dynamic range of the sensors or ADC instrumentation. A solution to this problem is to supply compensation fields with a number of compensation coils that equals the number of sensors. The physical positions and/or size of the compensation coils must be different from the applied field coils such that the applied field and compensation fields cancel each other at the sensor locations but do not cancel each other in the imaging volume. This can be accomplished by arranging the compensation coils with different offsets or angles with respect to the sensors than are used for the applied field coils.

In an embodiment with multiple AC bias fields from one or multiple bias field coils, the compensation coil gain may be separately adjusted for each of the bias field frequencies to null the bias field at the sensor for all of the frequencies simultaneously. The in phase and out of phase compensation gains are calculated separately when in phase and out of phase references are available. The in phase and out of phase components can also be calculated simultaneously using a single reference in quadrature.

In an embodiment with multiple AC bias fields and multiple sensors, there is the potential for direct coupling between the all of the compensation coils and all of the sensors. In this case, the compensation coil gains $G_{c1}$ to $G_{cN}$ must be adjusted simultaneously to null the total bias fields $H_{cT}$ at all frequencies and all sensor locations s1 to sN. The simultaneous adjustment of all compensation coils can be performed using direct linear inversion of a compensation coil-coupling matrix that tabulates the H contributions of the compensation coils c1 to cN at unity gain to each of the sensors s1 to sN. The compensation coupling matrix multiplied by the compensation gains results in the compensation field components measured by the sensors $$\begin{bmatrix} H_{s1,c1} & H_{s1,c2} & \ldots & H_{s1,cN} \\ H_{s2,c1} & H_{s2,c2} & \ldots & H_{s2,cN} \\ \vdots & \vdots & \ddots & \vdots \\ H_{sN,c1} & H_{sN,c2} & \ldots & H_{sN,cN} \end{bmatrix} \begin{bmatrix} G_{c1} \\ G_{c2} \\ \vdots \\ G_{cN} \end{bmatrix} = \begin{bmatrix} H_{cT@s1} \\ H_{cT@s2} \\ \vdots \\ H_{cT@sN} \end{bmatrix}. \qquad \text{Eqn. 22.}$$

The tuned compensation gains $G_{tc1}$ to $G_{tcN}$ are obtained by inverting the compensation coupling matrix and multiplying the resulting inverted matrix by the negative of the AC bias field strengths bT at the sensors s1 to sN $$\begin{bmatrix} G_{c1} \\ G_{c2} \\ \vdots \\ G_{cN} \end{bmatrix} = \begin{bmatrix} H_{s1,c1} & H_{s1,c2} & \ldots & H_{s1,cN} \\ H_{s2,c1} & H_{s2,c2} & \ldots & H_{s2,cN} \\ \vdots & \vdots & \ddots & \vdots \\ H_{sN,c1} & H_{sN,c2} & \ldots & H_{sN,cN} \end{bmatrix}^{-1} \begin{bmatrix} -H_{bT@s1} \\ -H_{bT@s2} \\ \vdots \\ -H_{bT@sN} \end{bmatrix}. \qquad \text{Eqn. 23.}$$

The resulting total field at the sensors from the bias coils $H_{bT}$ and compensation coils $H_{cT}$ will be approximately zero at the sensor locations s1 to sN $$\begin{bmatrix} H_{bT@s1} \\ H_{bT@s2} \\ \vdots \\ H_{bT@sN} \end{bmatrix} + \begin{bmatrix} H_{cT@s1} \\ H_{cT@s2} \\ \vdots \\ H_{cT@sN} \end{bmatrix} \approx \begin{bmatrix} 0 \\ 0 \\ \vdots \\ 0 \end{bmatrix}. \qquad \text{Eqn. 24.}$$

The bias coils and compensation coil fields will not sum to zero in general at other locations due to the different size and/or arrangement of the bias and compensation coils.

The compensation coupling matrix can also be calculated from measurements at multiple gain levels and then fit with a regression model to help reduce the effects of measurement noise. Nonlinear search algorithms such as nonlinear least squares, gradient descent, and the simplex method may also be used to perform the simultaneous adjustment of all compensation coils. The compensation coils also be tuned to bring the sensor readings to any arbitrary values other than zero to bias the sensors as desired. The compensation coil tuning can be tuned once for the purpose of reducing the directly coupled field. The compensation coils also could be tuned repeatedly to compensate for bias fields that are environment dependent or could be tuned continuously based on a reference magnetic field measurement for active noise cancelation.

Susceptibility Induced-Field Contribution at Each Voxel

The applied magnetic field strength at the centroid of each voxel is assumed to apply uniformly throughout the voxel, which is a reasonable assumption when the voxel size is small relative to its distance from the current loop of the electromagnet. The magnetization field from the voxel can be computed as the integral of a differential magnetic dipole over the volume of the voxel. The total magnetization field from the imaging volume is then obtained by summing the contributions of all the voxels.

The vector potential in SI units from a differential magnetic dipole outside of the source region is $$dA(r, m) = \frac{\mu_0}{4\pi}\left(\frac{dm \times r}{r^3}\right), \quad \text{Eqn. 25.}$$

where dm is the magnetic dipole moment from a differential volume element. The associated magnetic flux density dB in tesla from vector magnetic potential dA is the curl of the vector magnetic potential and is given as $$dB(r, m) = \nabla \times dA \quad \text{Eqn. 26.}$$

$$= \frac{\mu_0}{4\pi}\left(\frac{3r(dm \cdot r)}{r^5} - \frac{dm}{r^3}\right).$$

The magnetization field strength dM is $$dB(r, m) = \frac{dB(r, m)}{\mu_0}, \quad \text{Eqn. 27.}$$

where the differential magnetic dipole moment dm in eqn. 26 results from the volume magnetic susceptibility in the differential volume dV and the external field strength H in the volume $$dm = \chi_V H_V dV. \quad \text{Eqn. 28.}$$

For a rectangular cuboid voxel of size $(L_x, L_y, L_z)$ centered on the origin with $r=[x\ y\ z]$, $r=\sqrt{x^2+y^2+z^2}$ and $dV=dx\ dy\ dz$, the resulting magnetization field strength can be computed from the volume integral $$M(r, L, H) = \frac{\chi_V}{4\pi}\int_{-L_z/2}^{L_z/2}\int_{-L_y/2}^{L_y/2}\int_{-L_x/2}^{L_x/2}\left[\frac{3r(H \cdot r)}{r^5} - \frac{H}{r^3}\right]dx\,dy\,dz. \quad \text{Eqn. 29.}$$

If the magnetic field strength H is assumed constant within the voxel then the solution to eqn. 29 can be expressed in closed form. To make the resulting expression more compact, it is helpful to separate the solution into components $$M(r,L,H)=[M_x(r,L,H)\ M_y(r,L,H)\ M_z(r,L,H)], \quad \text{Eqn. 30.}$$

where $$M_x(r,L,H)=M_{x,x}(r,L,H_x)+M_{x,y}(r,L,H_y)+M_{x,z}(r,L,H_z), \quad \text{Eqn. 31.}$$

$$M_y(r,L,H)=M_{y,x}(r,L,H_x)+M_{y,y}(r,L,H_y)+M_{y,z}(r,L,H_z), \quad \text{Eqn. 32.}$$

$$M_z(r,L,H)=M_{z,x}(r,L,H_x)+M_{z,y}(r,L,H_y)+M_{z,z}(r,L,H_z). \quad \text{Eqn. 33.}$$

By symmetry of the rectangular cuboid, we will have $$M_{x,x}(r,L,H_x)=M_{z,z}(r_{yzx},L_{yzx},H_x), \quad \text{Eqn. 34.}$$

$$M_{y,x}(r,L,H_x)=M_{x,z}(r_{yzx},L_{yzx},H_x), \quad \text{Eqn. 35.}$$

$$M_{z,x}(r,L,H_x)=M_{y,z}(r_{yzx},L_{yzx},H_x), \quad \text{Eqn. 36.}$$

where $r_{yzx}=[y\ z\ x]$ and $L_{yzx}=(L_y,L_z,L_x)$. Similarly we have $$M_{x,y}(r,L,H_y)=M_{y,z}(r_{zyx},L_{zyx},H_y), \quad \text{Eqn. 37.}$$

$$M_{y,y}(r,L,H_y)=M_{z,z}(r_{zyx},L_{zyx},H_y), \quad \text{Eqn. 38.}$$

$$M_{z,y}(r,L,H_y)=M_{x,z}(r_{zyx},L_{zyx},H_y), \quad \text{Eqn. 39.}$$

where $r_{zyx}=[z\ x\ y]$ and $L_{zyx}=(L_z,L_x,L_y)$. The solution can now be completely expressed by the M-field components from an applied H-field in the z-direction. The x and y components are $$M_{x,z}(r, L, H_z) = \quad \text{Eqn. 40.}$$

$$\frac{\chi_V H_z}{4\pi}[f(-1, -1, -1, L_y - 2y) - f(-1, -1, +1, L_y - 2y) -$$
$$f(+1, -1, -1, L_y - 2y) + f(+1, -1, +1, L_y - 2y) +$$
$$\ldots f(-1, +1, -1, L_y + 2y) - f(-1, +1, +1, L_y + 2y) -$$
$$\ldots f(+1, +1, -1, L_y + 2y) + f(+1, +1, +1, L_y + 2y)]$$

and $$M_{y,z}(r, L, H_z) = \quad \text{Eqn. 41.}$$

$$\frac{\chi_V H_v}{4\pi}[f(-1, -1, -1, L_x - 2x) - f(-1, -1, +1, L_x - 2x) -$$
$$f(-1, +1, -1, L_x - 2x) + f(-1, +1, +1, L_x - 2x) +$$
$$\ldots f(+1, -1, -1, L_x + 2x) - f(+1, -1, +1, L_x + 2x) -$$
$$\ldots f(+1, +1, -1, L_x + 2x) + f(+1, +1, +1, L_x + 2x)],$$

where $$f(s_x, s_y, s_z, d) = \quad \text{Eqn. 42.}$$

$$\operatorname{atanh}\left(\frac{\sqrt{(L_x + s_x 2x)^2 + (L_y + s_y 2y)^2 + (L_z + s_z 2z)^2}}{d}\right).$$

The hyperbolic arctangent function is infinite when the argument is positive or negative unity, which occurs at geometric positions on the surface of the voxel, planes extending from the voxel surfaces, and lines extending from the voxel edges. The mathematical singularities at these locations always occur in positive-negative pairs so they can be avoided by defining $$\operatorname{atanh}\left(\frac{a}{b}\right) \equiv 0 \quad \text{Eqn. 43.}$$

when $$|a| - |b| < \varepsilon,$$

where $\varepsilon$ is the numerical precision of the computer. The z component of the M-field is $$M_{z,z}(r, L, H_z) =$$  Eqn. 44.

$$\frac{\chi_v H_z}{4\pi}[g(L_y - 2y, L_z - 2z, L_x - 2x, -1, -1, -1) +$$
$$\ldots g(L_y - 2y, L_z + 2z, L_x - 2x, -1, -1, +1) +$$
$$\ldots g(L_y + 2y, L_z + 2z, L_x - 2x, -1, +1, +1) +$$
$$\ldots g(L_y + 2y, L_z - 2z, L_x - 2x, -1, -1, +1) +$$
$$\ldots g(L_x - 2x, L_z - 2z, L_y - 2y, -1, -1, -1) +$$
$$\ldots g(L_x - 2x, L_z + 2z, L_y - 2y, -1, -1, +1) +$$
$$\ldots g(L_x + 2x, L_z + 2z, L_y - 2y, -1, +1, +1) +$$
$$\ldots g(L_x + 2x, L_z - 2z, L_y - 2y, -1, -1, +1) +$$
$$\ldots g(L_y - 2y, L_z + 2z, L_x + 2x, -1, +1, +1) +$$
$$\ldots g(L_y - 2y, L_z - 2z, L_x + 2x, -1, -1, +1) +$$
$$\ldots g(L_y + 2y, L_z - 2z, L_x + 2x, -1, +1, +1) +$$
$$\ldots g(L_y + 2y, L_z + 2z, L_x + 2x, +1, +1, +1) +$$
$$\ldots g(L_x - 2x, L_z + 2z, L_y + 2y, -1, +1, +1) +$$
$$\ldots g(L_x - 2x, L_z - 2z, L_y + 2y, -1, -1, +1) +$$
$$\ldots g(L_x + 2x, L_z - 2z, L_y + 2y, -1, +1, +1) +$$
$$\ldots g(L_x + 2x, L_z + 2z, L_y + 2y, +1, +1, +1)],$$

where $$g(n_1, n_2, d, s_x, s_y, s_z) =$$  Eqn. 45.
$$\text{atan}\left(\frac{n_1 n_2 d^{-1}}{\sqrt{(L_x + s_x 2x)^2 + (L_y + s_y 2y)^2 + (L_z + s_z 2z)^2}}\right).$$

and the subtraction of mathematical singularity pairs is avoided by defining $$\text{atanh}\left(\frac{a}{b}\right) \equiv 0$$  Eqn. 46.

when $$|a| - |b| < \varepsilon.$$

For voxels that are not centered on the origin, the magnetization field is evaluated with an offset term from the voxel center $(x_{0,voxel}, y_{0,voxel}, z_{0,voxel})$, where the magnetization field is $M(r_{voxel}, L, H)$ and $r_{voxel} = [x-x_{0,voxel}\ y-y_{0,voxel}\ z-z_{0,voxel}]$. The total magnetization field from the discretized tissue volume is the sum of the contributions of the voxels $$M_{tissue}(r) = \sum_{voxels} M(r_{voxel}, L, H).$$  Eqn. 47.

The magnetization field contribution $M_{tissue}(r)$ can be substituted into eqn. 3 to obtain the magnetic flux density at the SQUID coils as observed through eqn. 1 and eqn. 2. The result is the spatial distribution of the B-field resulting from the magnetic susceptibility of a single voxel. The spatial distribution was then numerically evaluated at each of the sensor 162 locations. These operations were then performed for all voxels, and the results are summed at each sensor location.

In an initial DC-SQUID configuration using a modified MAGNES-1 (Biomagnetic Technologies Inc., San Diego, Calif.), the majority of the sensors are first order, coaxial, spatial, magnetic SQUID gradiometers. Thus, the vector of induced field calculated above was dot multiplied with the unit normal vector of each sensing coil, and then the difference for each coil pair was calculated. This modeled value is equivalent to the measurement from the Magnes I.

The forward model discussed above can be written in the form $$\overline{A} \cdot \overline{X} = \overline{Y},$$  Eqn. 48 where $\overline{A}$ is the forward model and has the dimensions sensors by voxels, $\overline{X}$ is the matrix of magnetic susceptibilities and is a column vector that is voxels long, and $\overline{Y}$ is the measurement column vector that is sensors long. The matrix accounts for the applied field, the geometry and discretization of the source space, and the sensor geometry.

Tomography

The implemented method evaluated was the Moore-Penrose pseudoinverse. This method arrives at a unique inverse matrix by adding the additional constraint that the L2 norm of the estimated susceptibility vector, $\overline{X}$, is minimized. The qualitative result of this constraint is to preferentially weight estimates of the magnetic susceptibility nearer to the sensors. This trend is accounted for by the fact that the field strength of a magnetic dipole falls off as $$\frac{1}{r^3};$$

therefore, for a given sensor reading that could potentially be the result of two different dipole locations, the dipole nearer to the sensor is preferentially selected because the magnitude of that dipole that is required to account for the measurement is less than that of the dipole that is further from the sensor, minimizing the L2 norm. The potential of this modality was evaluated by simulating a three axis applied field system consisting of six coils (two per axis) and then performing a reconstruction with 0.5 cm voxels.

We performed experiments that show that the spatial and temporal recording of magnetic susceptibility for a MST tomographic image using low power applied magnetic fields and a MEG tomographic image in a configuration usable for human studies is possible using the same equipment. Images from both modalities can be displayed separately, or a combined image having colors indicative of data obtained from both modalities can be generated. Such a composite image could be termed a MEG-MST image, and would have an MEG component representing neural activity and a MST component representing tissue composition. Additionally, the computational analysis of magnetic susceptibility tomographic reconstruction within the MEG's imaging space should result in images with good temporal and spatial characteristics. The combination of these studies implies that a high fidelity spatiotemporal tomographic image is possible with this configuration.

It is anticipated that differences between measured and applied fields representative of induced fields in materials within the measurement volume are mapped to produce tomographic images by processor 124 executing magnetic susceptibility tomography (MST) routines from memory 122. The MST routines include machine readable instructions for directing processor 124 to divide the measurement volume into voxels, to determine field strength differences between applied and measured magnetic fields at each voxel, and to construct tomographic images displaying information derived from those field strength differences as MST images representative of magnetic susceptibility at each voxel. In a particular embodiment, magnetic susceptibility is derived from those field strength differences and displayed as MST images.

It is also anticipated that the field strength difference and/or magnetic susceptibility voxels of the MST images described above and the field strengths of voxels of the MET routines may be represented together as a composite tomographic image by composite tomography routines in memory of the processor.

Improving Sensitivity and Resolution

In order to increase sensitivity, and improve tomographic reconstruction by identifying contributions of field and susceptibility at particular sensor elements 162 from particular bias coils 166, we propose using alternating current, instead of direct current, in the bias coils to produce alternating magnetic fields within the measurement volume.

In an embodiment the bias coils 166 are driven by drivers 126 not with direct current, but with an AC modulating current, and this current is measured with a high precision analog to digital converter in data acquisition unit 120. Each sensor 166 is also read with a high-precision analog to digital converter in data acquisition unit 120, and measurements from the sensors 166 are correlated using a multivariate linear regression operating in the processor 124 to detect small changes in amplitude over several cycles of the AC modulating current.

It is expected that the combination of linear regression comparing current in bias coils to sensor measurements with AC modulation will provide greater sensitivity to minute induced fields, and changes in those minute fields, than obtainable with our previous DC SQUID measurements.

Further, by operating each of particular bias coils at a different frequency, and separating detected magnetic field signals from the sensors according to frequency, we can identify an induced field component at each sensor that is associated with each of the particular bias coils.

For example, if we have four bias coils and eight sensors, a first bias coil is driven at a first frequency, the second at a second frequency, the third at a third frequency, and the fourth at a fourth frequency. At each sensor, the received signals representing detected magnetic fields are individually correlated against the first, second, third, fourth, and in embodiments using additional frequencies, the additional signals measured at each bias coil, including a first and a second bias coil of the bias coils, to give an induced field contribution of each bias coil at each sensor. In a particular embodiment, the received signals representing detected magnetic fields are digitized and digitally correlated by linear regression against the first, second, third, fourth, and in embodiments using additional frequencies the additional, digitized signals measured at each bias coil to give an induced field contribution of each bias coil at each sensor. In an alternative embodiment, a separate lock-in amplifier is provided at two or more of the sensors for each of the first and second, or more, operating frequencies, thereby allowing determination of induced field contributions of each bias coil at each of these sensors. This system is expanded by adding additional bias coils operating at additional, individual, frequencies, and by adding additional sensors. It is anticipated that embodiments may have several hundred sensors and several dozen bias coils, where each bias coil operates at a different frequency. We term this AC induced-field measurement with linear regression and frequency-domain separation of individual bias coil contributions.

In addition to improving sensitivity, the induced field component of each bias coil at each sensor is used by processor 124 to further disambiguate and enhance resolution during enhanced tomographic reconstruction.

When using many bias coils, the summation of the bias fields from all active coils must be within the operating range of the SQUID or fluxgate sensor. Although this may appear to significantly limit the number of bias coils that may be used, the distance of the bias coils relative to the sensor reduces the excitation field at the sensor and mitigates the potential problem. The use of compensation coils also mitigates problem of direct coupling of the applied or bias field to the sensors by locally cancelling the applied fields at the sensor locations. The orientation of the bias coils is also chosen so that the field experienced by each sensor is substantially less than the field that targets the imaging region of interest. While it is essential that the applied field from the bias coils excite the tissue, the function of the sensor is to read the signal component from the excited tissue so having reduced direct coupling from the bias coils to the sensors is beneficial.

Some embodiments, both of SQUID, Atomic Magnetometer, and Fluxgate types, have bias coils and sensors that are grouped to reduce the total number of independent bias signal generators and independent AC operating frequencies required for MST. In a particular embodiment, there are two groups, one associated with each hemisphere of the brain. Each group has one bias coil operating at each AC stimulus frequency. In this embodiment, signals from sensors associated with the left hemisphere are coupled through single-pole double-throw relays, or equivalent devices, to the lock-in amplifiers 119 during a first MST measurement, then the relays are switched and sensors associated with the right hemisphere are coupled through the relays to the lock-in amplifiers 119 during a second MST measurement. In other alternative embodiments, other groupings of coils and sensors may be used.

Combined Magnetoencephalographic and Magnetic Susceptibility Imaging Instrument Some available magnetoencephalographic machines using SQUID sensors have bandwidth of as much as 5 kHz, others have bandwidth of 1 MHz, 100 MHz or as high as 1 GHz. The useful bandwidth for magnetoencephalography is, however, primarily zero to 200 Hz. In an embodiment, we apply the bias coils 166 to a head-surface of a helmet of such a machine.

In addition to AC induced-field measurement with linear regression and frequency-domain separation of individual bias coil contributions, we use AC currents of greater than 200 Hz in all bias coils of the machine. Further, we digitally low-pass filter data read through the data acquisition system 120 from sensors 162 in processor 124 to separate a magnetoencephalographic signal from the AC magnetic susceptibility signal described above with reference to AC induced-field measurement with linear regression and frequency-domain separation of individual bias coil contributions.

In this way, our system is capable of simultaneously acquiring magnetoencephalographic and magnetic susceptibility data suitable for MET and MST. We use the term frequency-domain separation of MET and MST herein to indicate separating MET and MEG data by recording MEG data at low frequencies, such as below a threshold frequency like 200 Hz, while simultaneously capturing MST data by AC susceptometry as described above using bias coils driven at higher frequencies, such as above a threshold frequency like 200 Hz. In other embodiments, a higher threshold frequency such as 1000 Hz may be used.

For MST of hemodynamics from local regions of the brain where the total quantity of brain tissue involved is on the order of 100 mm$^3$, and the evoked hemodynamics are on the order of a few percent change in blood oxygenation, a signal-to-noise ratio of $10^{10}$ may be required. The required signal-to-noise ratio is lowered by the use of compensation coils by a factor of 100, or 1000 or more depending on the noise characteristics and precision of the compensation coil and circuitry. While it is unlikely that any magnetometer will have this type of performance, this signal-to-noise ratio is achievable by employing a precise bias oscillator signal and an analog or digital lock-in amplifier. Lock-in amplifiers use the reference signal to measure frequency and phase locked signal component of interest even when noise is much higher than the signal itself. The achievable level of signal-to-noise amplification from a lock-in amplifier is on the order of $10^3$ to $10^6$, depending on frequency precision and phase stability of the reference signal, and the frequency bandwidth of the magnetometer. Reference signals with stability up to 1 part per billion are readily available. The bandwidth of the magnetometer is thus the limiting factor on the signal-to-noise amplification of the lock-in amplifier.

The SQUIDs themselves have a bandwidth of up to 1 GHz but the bandwidth of the associated SQUID electronics is typically limited by the particular signal transmission lines and circuits in the system. Some SQUID MEG systems are designed to operate with a bandwidth of 100 MHz or more.

Portability and Operating Expense Reduction

The embodiments heretofore discussed use SQUID-based magnetic sensors. These require cryogenic liquids for operation, in one embodiment using traditional SQUIDs requiring liquid helium, and in an alternative high temperature embodiment using less-sensitive high-temperature SQUIDs requiring liquid nitrogen. While liquid nitrogen is lower in cost than liquid helium, both are inconvenient and expensive, and require extensive and heavy thermal insulation including vacuum-insulated Dewar's.

Embodiments Based on Fluxgates

Figure 6:
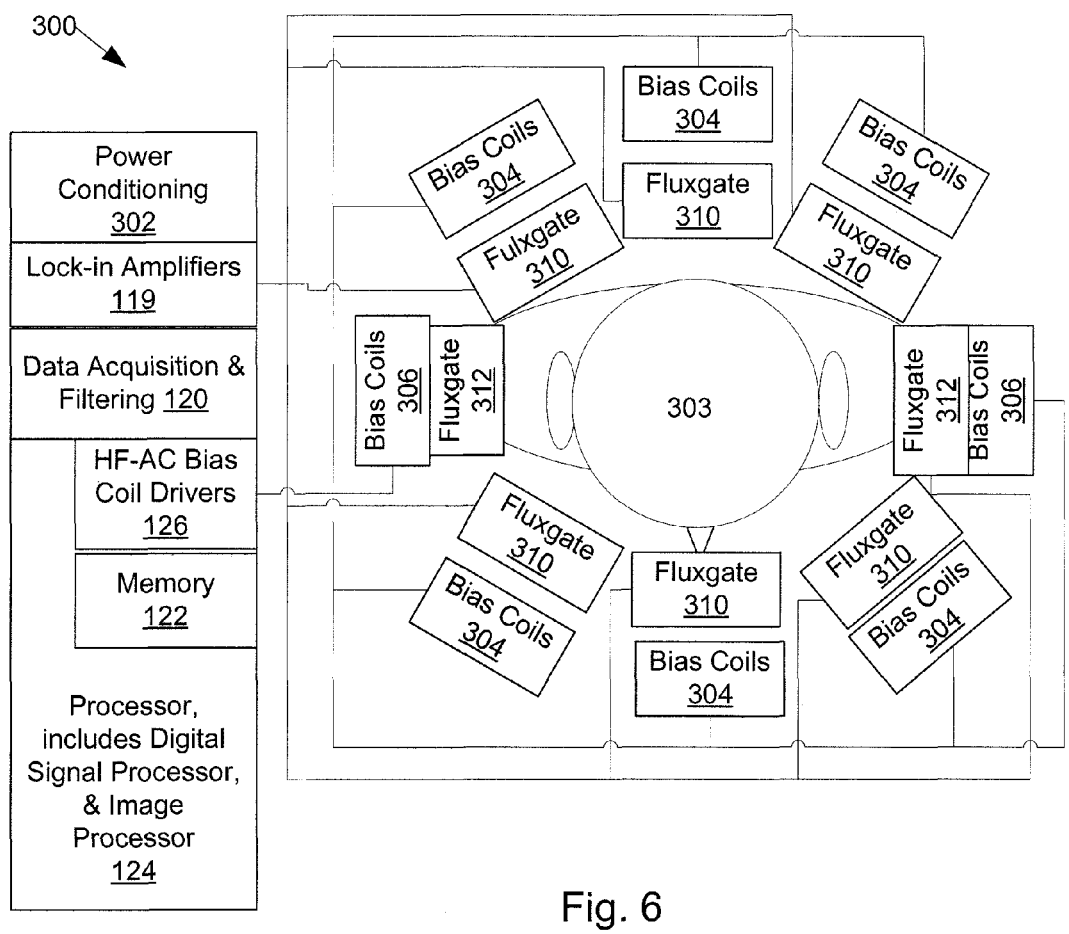
FIG. 6 illustrates an embodiment of an MST machine based on fluxgate magnetometers.

In an alternative embodiment 300, (FIG. 6), no shielded room is provided since only induced-field measurements are performed for MST of tissue and/or MST of nanoparticle concentrations, while the very low magnetic fields of MEG are not measured. In this embodiment, power conditioning apparatus 302 provides clean power to lock-in amplifiers 119, data acquisition 120, and bias-coil drivers 126 to prevent interference from power-line ripple. Bias-coil drivers 126 provide current to drive bias coils 304, 306 that provide AC magnetic fields of known intensity to tissue and/or nanoparticle concentrations in a subject or portion of a subject, such as a subject's head 303. The bias-coil drivers 126 operate under control of processor 124 to provide particular patterns of AC magnetic fields that will permit processor 124 to localize concentrations of paramagnetic materials in subject 303

Sensitive flux-gate sensors 310, 312 are provided to perform AC measurements of magnetic fields applied to and induced within subject 303. In embodiments with analog lock-in amplifiers, readings from the flux-gate sensors 310, 312 are amplified with lock-in amplifiers 119, digitized by data acquisition and filtering unit 120 coupled to lock-in amplifiers 119, and processed in processor 124 as described above to recover signals from the minute induced magnetic fields and to perform frequency-domain separation of individual bias coil contributions to the induced fields. In embodiments with digital lock-in amplifiers, readings from flux-gate sensors 310, 312 are amplified, digitized by data acquisition and filtering unit 120, and further processed by digital lock-in amplifiers coupled to data acquisition and filtering unit 120 before further processing in processor 124 to recover signals from the minute induced magnetic fields and to perform frequency-domain separation of individual bias coil contributions to the induced fields.

Fluxgates have a bandwidth of typically 1000 Hz but sometimes as high as 3000 Hz, this high-frequency capability permits use of AC lock-in amplification and digital correlation techniques to quantify signals from minute induced fields. In some embodiments, measurements of induced fields may be performed with bias coils energized in different patterns, and induced field measurements from each pattern of bias coil energization are combined to provide accurate MST reconstruction, for example bias coils 306 may be energized with bias coils 304 turned off, then bias coils 304 energized with bias coils 306 turned off, to provide additional spatial resolution. Once the induced fields for all sensors 310, 312 are quantified, these measurements are used to perform MST tomographic reconstruction as heretofore described.

In another alternative embodiment, a shielded room may be provided to gain additional noise reduction.

It is believed that the regression signal-recovery technique heretofore discussed will permit operation for MST with flux-gate sensors in place of SQUIDs and thus permit enhanced portability and reduced operating costs by eliminating the need for cryogenic liquids.

Embodiments based on Atomic Magnetometers

Figure 8:
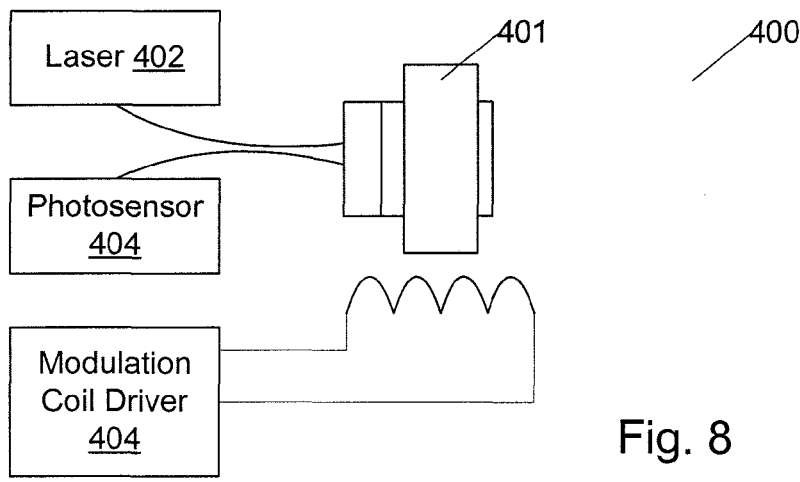
FIG. 8 illustrates a remotely located laser and photodetector of a cesium atomic magnetometer.

CSAM devices 400, as illustrated in FIG. 8, have a cell 401 filled by an alkali metal vapor, such as cesium vapor, and operate by measuring changes in light transmitted to a photosensor from a polarized incident laser beam. Additional optical components exist in each cell, such as diffraction gratings, that are not shown in FIG. 8. While in some embodiments of CSAM devices, the incident laser beam is provided by an infrared laser mounted adjacent the vapor cell, in order to reduce noise from stray magnetic fields the incident laser beam may be provided through an optical fiber from a remotely located laser 402. Similarly, while in some embodiments of CSAM devices, the response is measured by a photodetector mounted adjacent the vapor cell, the response may be measured through an optical fiber by a remotely located photosensor 404. The alkali-metal vapor, such as cesium vapor, in the cell may also be heated to vapor state by radiation transmitted through an optical fiber from a remotely-located laser.

Figure 1C:
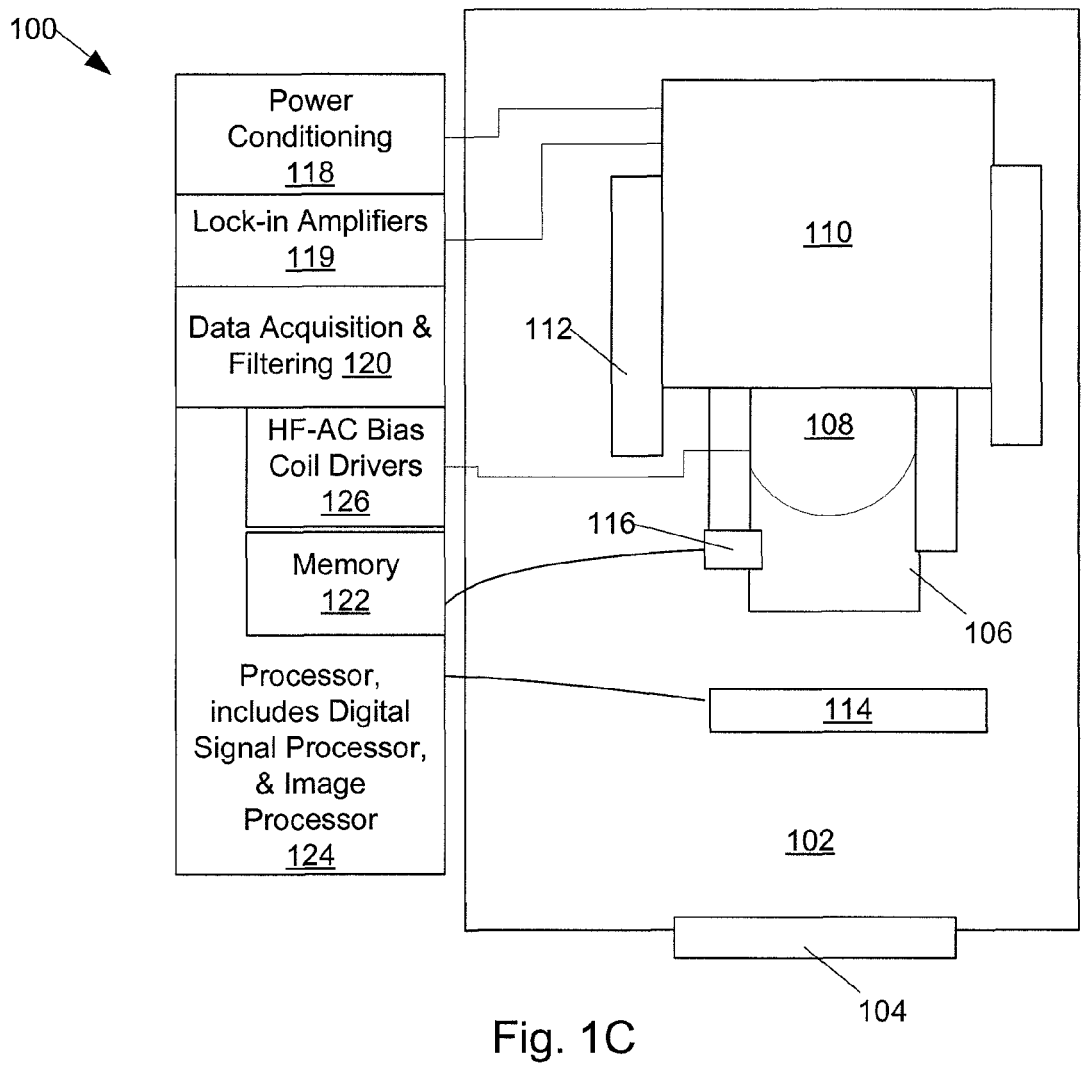
FIG. 1C illustrates schematically a system for providing magnetoencephalography (MEG) and magnetic susceptibility tomographic (MST) images.
Figure 1D:
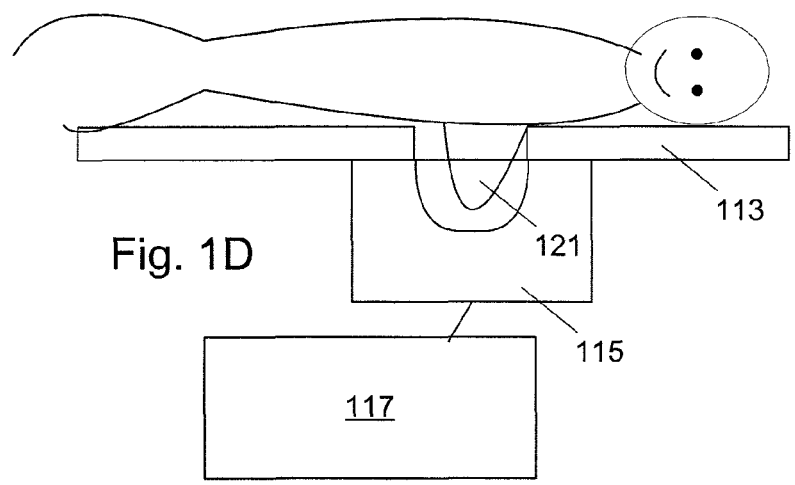
FIG. 1D illustrates schematically an inverted MST system having magnets and sensors in a cup arranged beneath a table and adapted for breast imaging.
Figure 1E:
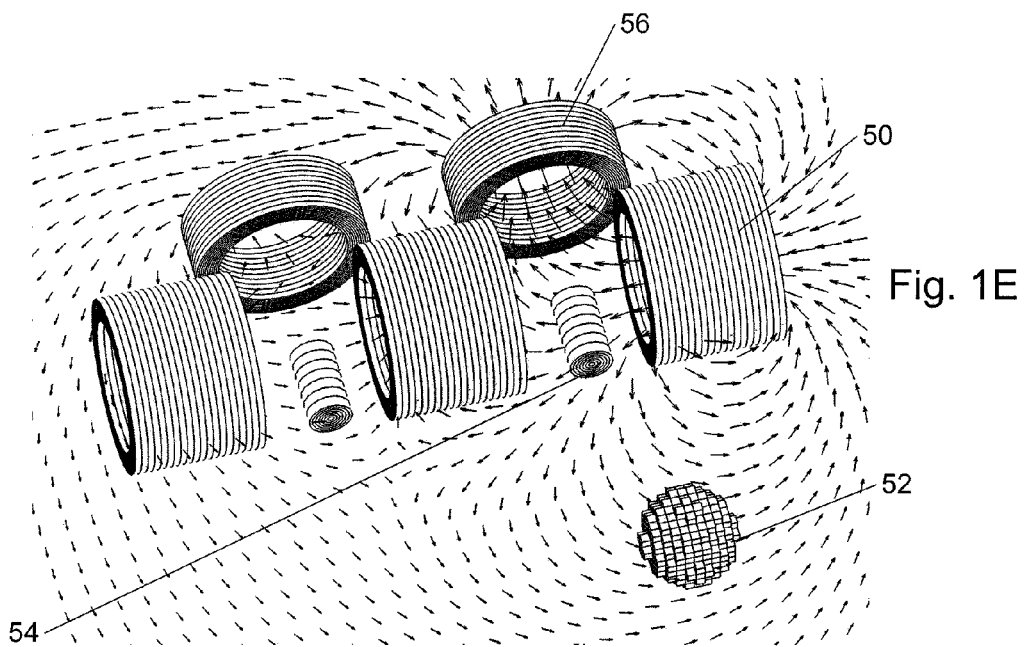
FIG. 1E illustrates sensing a field developed in the magnetically susceptible material while both a bias field is applied, and a compensating field is applied, with nulled fields at a sensor.
Figure 7:
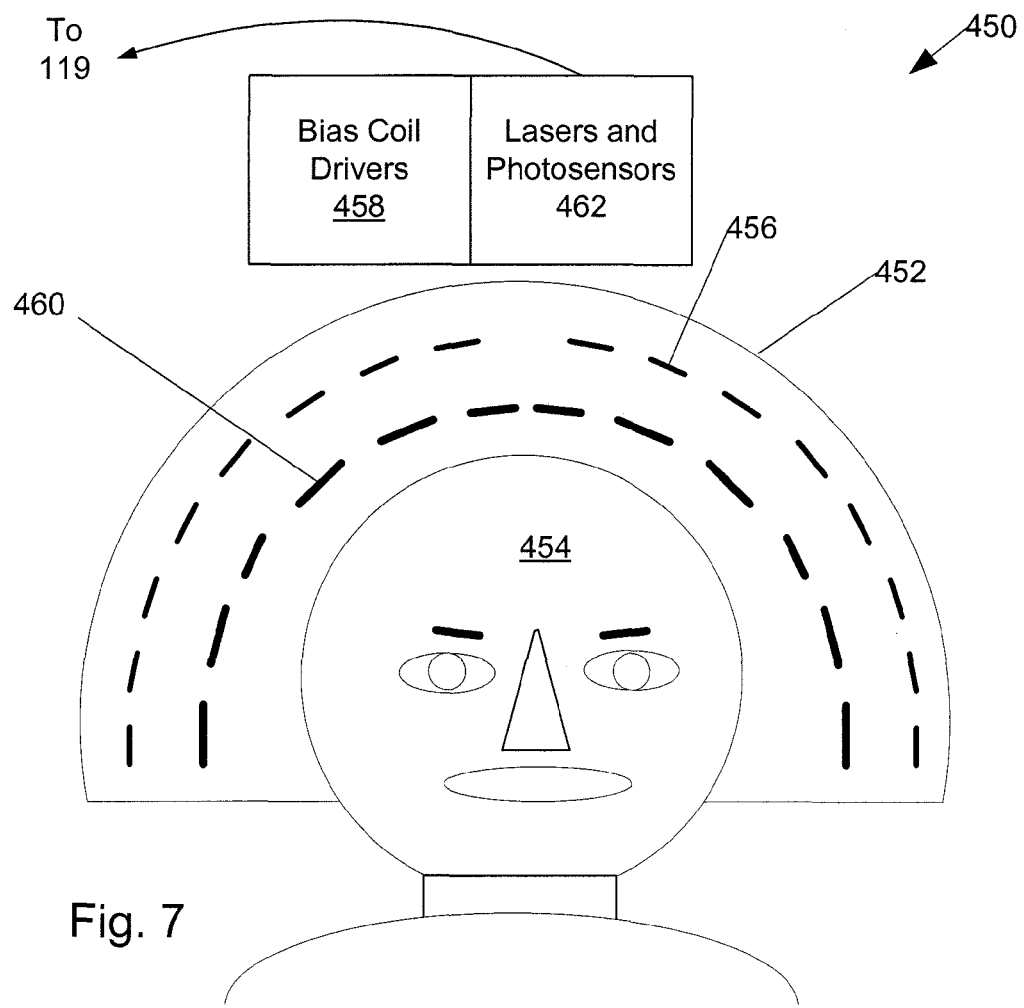
FIG. 7 illustrates an embodiment of a sensor helmet of an MEG-MST machine based on atomic magnetometers.

An embodiment 450 of the MEG-MST resembling that of FIG. 1C but using atomic magnetometers uses a sensor helmet as illustrated in FIG. 7. This helmet has a magnetic shield 452 fabricated of a magnetic material and configured to surround a head 454, or other portion of anatomy of interest, of a subject. Within the shield 452 are an outer shell of bias coils 456, each of which is coupled to a driver in a bias driver module 458 attached to the shield 452. Bias coils 456 are configured to apply alternating-current magnetic fields to induce induced magnetic fields in the magnetically susceptible materials, or magnetic nanoparticles, within head 454. An inner layer within the bias coils 456 are located an inner shell of atomic magnetometers 460. Bias coils of each atomic magnetometer 460 are coupled to drivers in bias driver module 458 by shielded wires (not shown), and each magnetometer 460 is coupled to a laser and a photosensor in lasers and photosensors module 462 by an afferent and an efferent optical fiber (not shown for simplicity). The bias drivers in bias driver module 458 operate under control of processor 124, as illustrated in FIG. 1C to provide a bias that cancels the earth's magnetic field during MEG operation, and to provide bias for inducing magnetic fields within magnetically susceptible materials of head 454 during MST operation.

Signals received from each magnetometer 460 through associated photosensors in lasers and photosensors module 462 are coupled as inputs to lock-in amplifiers 119, whence they are amplified, digitized, and processed as heretofore described with reference to the SQUID embodiment described above with reference to FIGS. 1C and 2. Tomographic images generated from MEG and MST operations are generated by processor system 124, displayed on a display device (not shown), and transmitted over a network to an electronic medical records (EMR) database server (not shown) where they are entered into an EMR record of the particular subject.

In an alternative embodiment, bias coils 456 and magnetometers 460 are attached to an elastomeric cap configured to be worn on head 454.

The CSAM described by Sander has a bandwidth of 150 Hz but this bandwidth will increase in future atomic magnetometers. A high-bandwidth CSAM will permit use of high frequency AC susceptometry and lock-in amplifiers to further increase dynamic range and sensitivity to weak MEG and MST signals.

Noise Comparison for Atomic Magnetometer, Fluxgate, and SQUID

The effective capability of a particular magnetometer for MST can be calculated as the range-to-noise ratio times the square root of the bandwidth divided by the desired hemodynamic sampling rate. Using a threshold of 10 billion for MST of hemodynamics in the brain and a 10 Hz sampling rate for the hemodynamics the bandwidth requirement can be evaluated from: (range-to-noise ratio)×sqrt[(bandwidth)/(sample rate)]≥$10^{10}$. The range-to-noise ratio for a SQUID MEG is $5.7×10^6$, for a fluxgate is $1.0×10^7$, and for a CSAM is $5.0×10^6$. The minimum bandwidth requirement for a SQUID system is 31 MHz, for a fluxgate it is 10 MHz, and for a C SAM system is 40 MHz. The bandwidth requirement is within the known operating range of a SQUID MEG. For the CSAM, the bandwidth is too high for current models but we expect this will be overcome in newer models very soon. The bandwidth requirement is too high for the fluxgate since this sensor type does not operate in the MHz range. Fluxgates could, however, still be useful for MST of large changes in hemodynamics from larger regions of the brain that are persistent or slow to change in time, such as from a stroke. For example, for a hemodynamic change that is 10 times larger than a typical small evoked response and a hemodynamic sampling rate of 0.1 Hz, the fluxgate minimum bandwidth requirement is 1000 Hz, which is well within its capability.

There are two competing factors for an MEG-MST imaging system. One is the absolute noise floor of the sensor and how that relates to the ability to detect brain activity and the other is the ability to detect minute magnetic susceptibility changes from blood in the brain. Presently available SQUID sensors satisfy both requirements, present fluxgate sensors satisfy the MST requirement but are only capable of measuring the very largest of MEG brain rhythms. CSAM presently meets the MEG requirements but would require time averaging for MST requirements. Modifications to the SQUID system to achieve higher bandwidth will further improve its MST performance and future improvements to CSAM could make it viable for MST and MEG. All three sensors are easily capable of measuring MST signals from magnetic nanoparticles. All three sensors could thus be used for MST if magnetic nanoparticles are used as a contrast agent.

Other Magnetic Field Sensors

Alternative types of magnetic field sensors may be used in applications where larger magnetic field signals are present such as with magnetic nanoparticle taggants or where magnetic nanoparticles are injected into a subject as a contrast agent, treatment agent, or both. Alternative types of magnetic field sensors are induction coils, Hall effect sensors, and magneto-resistive sensors. These sensors types may be discrete sensors, chip based sensors, or manufactured onto a printed circuit board in an array configuration.

Other Variations

The term sensitive magnetic sensors as used herein therefore includes both sensitive flux-gate sensors, atomic magnetometers, and SQUID sensors.

In particular embodiments, including some of those that operate outside a shielded room, it may be desirable to apply a superimposed direct and alternating current to one or more bias coils. For example, an embodiment may provide to one or more of its coils a direct current sufficient to generate a magnetic field sufficient to cancel the earth's magnetic field, with a small alternating current determined to be sufficient to cancel interference from nearby power distribution lines, with an alternating current at a particular frequency superimposed on the direct current that provides an alternating magnetic field for sussceptometry. This embodiment may also provide a reference at that particular frequency to lock-in amplifiers for low-noise amplification of signals from sensitive magnetic sensors disposed along with the tissue being examined within the alternating magnetic field. For purposes of this document, driving circuits that provide a superimposed direct and alternating current to a bias coil are referenced as providing an alternating current to the bias coil.

In some embodiments, particularly when the sensor bandwidth is low and time resolution requirements are modest, it may be desirable to use time multiplexing rather than frequency encoding to uniquely identify the field contributions from particular bias coils and their interactions with a magnetically susceptible sample. In the time multiplexing approach, one bias coil is activated at a time in a predetermined sequence. Knowledge of the time sequence is then used to parse the measured signals into contributions from each of the bias coils interacting with the sample. A complete sequence of parsed signals can then be used in tomographic image reconstruction routines in the memory of a processor.

In particular embodiments where the susceptibility properties of the sample medium are strongly frequency-dependent, it is anticipated that multiple MST tomography images of the same sample medium may be reconstructed. In an embodiment, one MST image is reconstructed using a set of low frequency AC bias coil frequencies, a second MST image is reconstructed using a set of medium frequency AC bias coil frequencies, and a third image is reconstructed using a set of high frequency AC bias coil frequencies, wherein each of the three images contains different magnetic susceptibility information content about the sample medium. In a particular embodiment, the three images are differenced by image processor 124, so that high-low frequency difference images can be displayed, thereby highlighting regions with high difference between high and low frequency susceptibility. In some embodiments, for example when the sample medium has time varying material properties, the use of three sets of AC bias coil frequencies may be multiplexed in time so that a time series of images is obtained using the low, medium, and high frequencies is cyclically obtained over time. In a particular embodiment, an initial set of images is stored, and differences determined between the initial set of images and a later set of images by image processor 124, so that time difference images can be displayed, thereby highlighting regions where susceptibility has changed; the susceptibility changes may, for example, result from introduction of a magnetic nanoparticle contrast agent into the medium.

It is anticipated that the systems herein described may capture data associated with MST sufficiently quickly to provide dynamic MST tomographic image series producing an display of changes to magnetic susceptibility in the head with an effective frame rate greater than that achievable with fMRI images, and thereby enable functional MST, or fMST. Although the dynamic MST tomographic images will provide useful information regarding brain function even at low effective frame rates of several frames per minute, in a particular embodiment, dynamic MST with an effective frame rate of at least five hertz is expected.

It is anticipated that the apparatus herein described may be adapted for determining magnetic susceptibility tomographic images from a whole body, or from other portions of a body than the head alone as heretofore described, although such embodiments may not be able to simultaneously provide magnetic encephalographic information.

Although the apparatus above described for MST is not compatible with simultaneous fMRI because of the intense and varying magnetic fields required for fMRI, it is anticipated that the apparatus heretofore described is compatible with simultaneous functional neuroimaging fNIRS. We have already demonstrated compatibility of simultaneous fNIRS with DC-SQUID-based MET and magnetic susceptibility measurement. We expect to be able to perfaini simultaneous fNIRS and MST using AC bias techniques as above described, as well as simultaneous fNIRS, MST, and MET using AC bias and frequency domain separation of MST and MET data as herein described. Further, should electrodes and conductors be carefully chosen to avoid electrodes or wiring containing magnetic metals, we expect to be able to perform simultaneous electroencephalography (EEG) and MST, simultaneous EEG, MST, and MET, simultaneous fNIRS, EEG, MST, or simultaneous fNIRS, EEG, MST, and MET, or any other combination of fNIRS, EEG, MST, and MET.

Enhanced Spatial Encoding for Improved MST Resolution

A specific advantage of the proposed use of multiple bias coils and multiple magnetic sensors is that spatial encoding may be performed to enhance the tomographic resolution beyond what is possible by the linear combination of multiple independent sensors. The spatial encoding method relies on selection of the frequencies of pairs of bias coils that are spatially separated to achieve beat frequencies that result from constructive and destructive interference in the spatial region between the two bias coils. This interference signal will contain new information for spatial encoding if the combination of applied fields results in a nonlinear phase and/or amplitude response by the magnetically susceptible material. Such a nonlinear response can arise from magnetic field saturation effects and also from nonlinearity in the magnetization frequency response of some materials. The spatial extent of the interference field will be focused in the region between the coils because the field magnitude from each coil decays with distance from the coil. The sensitivity region of the interference field is localized to the product of the field magnitude map from the two coils. The spatial extent of an interference field will in general be more localized (have smaller spatial extent) than the field pattern from an individual coil. Measuring the susceptibility response associated with the interference field will therefore enable higher resolution tomographic reconstructions over the use of individual coils.

Achieving improved resolution from spatial encoding at the desired bandwidth for time variation in susceptible material imparts additional constraints on the selection of the bias coil frequencies. Specifically, the beat frequencies must be higher than the desired sampling rate to capture time variations in the susceptible material. For example, if a sampling rate of $f_{hemodynamics}=10$ Hz is desired for imaging hemodynamics and the frequency of the first bias coil $f_{bias1}=1000$ Hz, then the frequency of the second bias coil must be $f_{bias2} \geq 1010$ Hz. Suppose that $f_{bias2}=1010$ Hz was chosen. The beat frequencies for the interference field between the coils would be $f_{beat}=f_{bias2}-f_{bias1}=10$ Hz and 2010 HZ. The lower of the two beat frequencies is of interest $f_{beat}=10$ Hz. The beat frequency acts as a virtual bias coil that applies an AC magnetic field to the spatial region of the interference field.

The magnetization information from the beat frequency interference field may be extracted from the signal of any magnetic sensor that is within range of the applied fields. The signal measured by the magnetic sensor s is separately notch filtered at the bias field frequencies $f_{bias2}$ and $f_{bias1}$. The notch filters are needed to isolate the beat frequency of the two bias coils in question with respect to all other potential bias coil pairs. The resulting signals $s_1$ and $s_2$ are then multiplied $s_1 \cdot s_2$ to demodulate the beat frequency from bias field frequencies $f_{bias2}$ and $f_{bias1}$ down to the beat frequency $f_{beat}$. The signal $s_1 \cdot s_2$ is then analyzed using a lock-in amplifier or linear regression where the reference signal is an oscillator at the beat frequency $f_{beat}$. The low pass filter in the lock-in amplifier or linear regression method must have a cutoff frequency that satisfies $f_c \leq f_{beat}$, which in this example could be a cutoff of 10 Hz to enable a sampling rate of 10 Hz on the time variation of susceptibility due to hemodynamics. An alternative approach to the interference signal analysis is to square the magnetic sensor $s^2$ and then analyze the results using a lock-in amplifier or linear regression with a reference signal that is the product of the two bias coil oscillators $s_{ref}=s_{1ref} \cdot s_{2ref}$. Using a reference signal that is the product of the two bias coil references will isolate the beat frequency of the two bias coils in question with respect to all other potential bias coil pairs.

A major advantage of this proposed spatial encoding method is that the effective number of bias coils will increase proportionally to the number of coils squared rather than linearly as the number of bias coils. If the number of bias coils is N, the effective number of bias coils from the spatial encoding approach will be $N_{effective}=N+(N^2-N)/2=(N^2+N)/2$. Tomographic resolution is proportional to the effective number of bias coils multiplied by the number of magnetic field sensors S that are within range of imaging volume. The number of unique measurements is what limits the number of voxels that may be uniquely reconstructed in the tomographic operations. Without the spatial encoding approach, the resolution limit is the product SN. With the proposed spatial encoding approach, the resolution limit is $S(N^2+N)/2$. For a large imaging volume, some magnetic field sensors will not sense from the entire imaging volume so in practice the resolution limit will be somewhat lower but the relative gain in tomographic resolution from the spatial encoding will be preserved.

Figure 9:
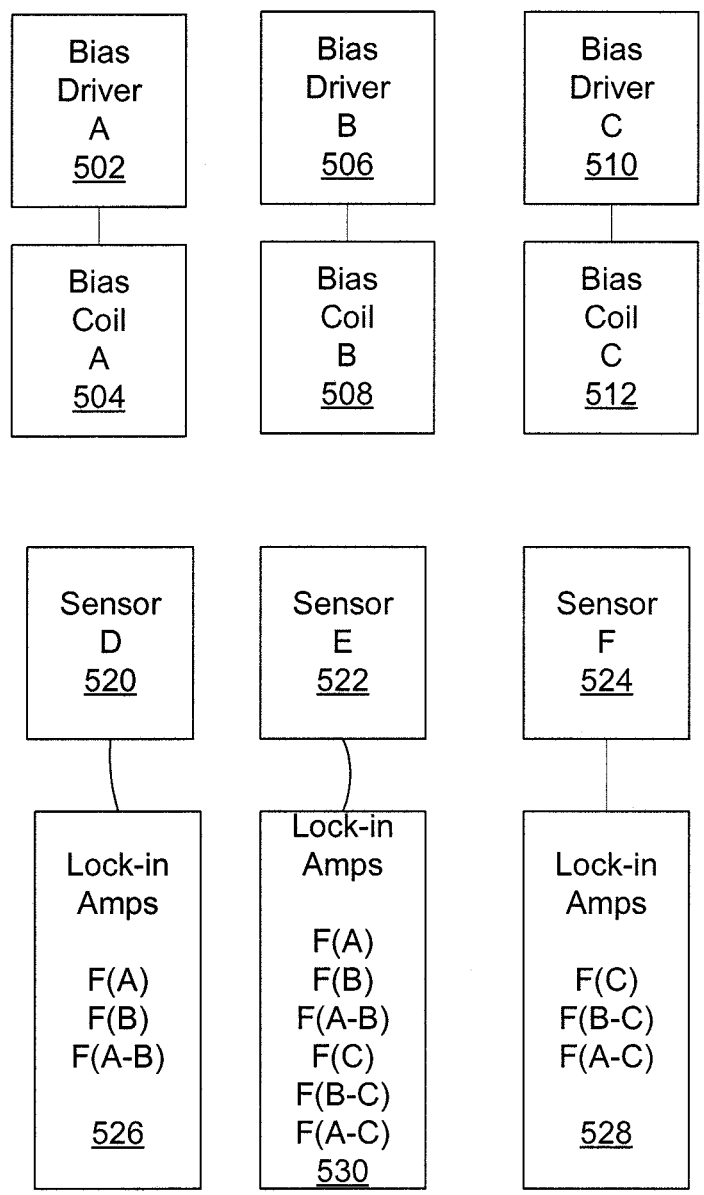
FIG. 9 illustrates multiple lock in amplifiers (or regression frequency pairs) provided to enhance spatial resolution between adjacent sensors and bias coils.

Therefore, in some embodiments as illustrated in FIG. 9, signals received at each sensor, such as sensors 520, 522, 524 are digitally correlated by linear regression against each, such as a first, second, third, and fourth, or more frequency applied to bias coils 504, 508, 512, where each bias coil is individually driven at one frequency by bias drivers 502, 506, 510. Further, in some of these embodiments, signals received at each sensor are digitally correlated by linear regression at beat frequencies, such as difference or sum frequencies (such as frequency A applied to bias coil 504 and frequency B applied to bias coil 508), of frequency pairs applied to adjacent bias coils to give a spatially-resolved induced field contribution of each bias coil at each sensor (such as frequency A-B). Where sensors are adjacent to multiple bias coils such as sensor 522, induced field contributions are measured at multiple frequency difference pairs, such as frequencies A-B and B-C. In an alternative embodiment, a separate lock-in amplifier 526, 528, 530 is provided at two or more of the sensors for each of the first and second, or more, operating frequencies, and at each difference frequency of interest at those sensors, thereby allowing determination of induced field contributions of each bias coil at each of these sensors by selectively amplifying signals that may appear at the beat frequencies.

Figure 10:
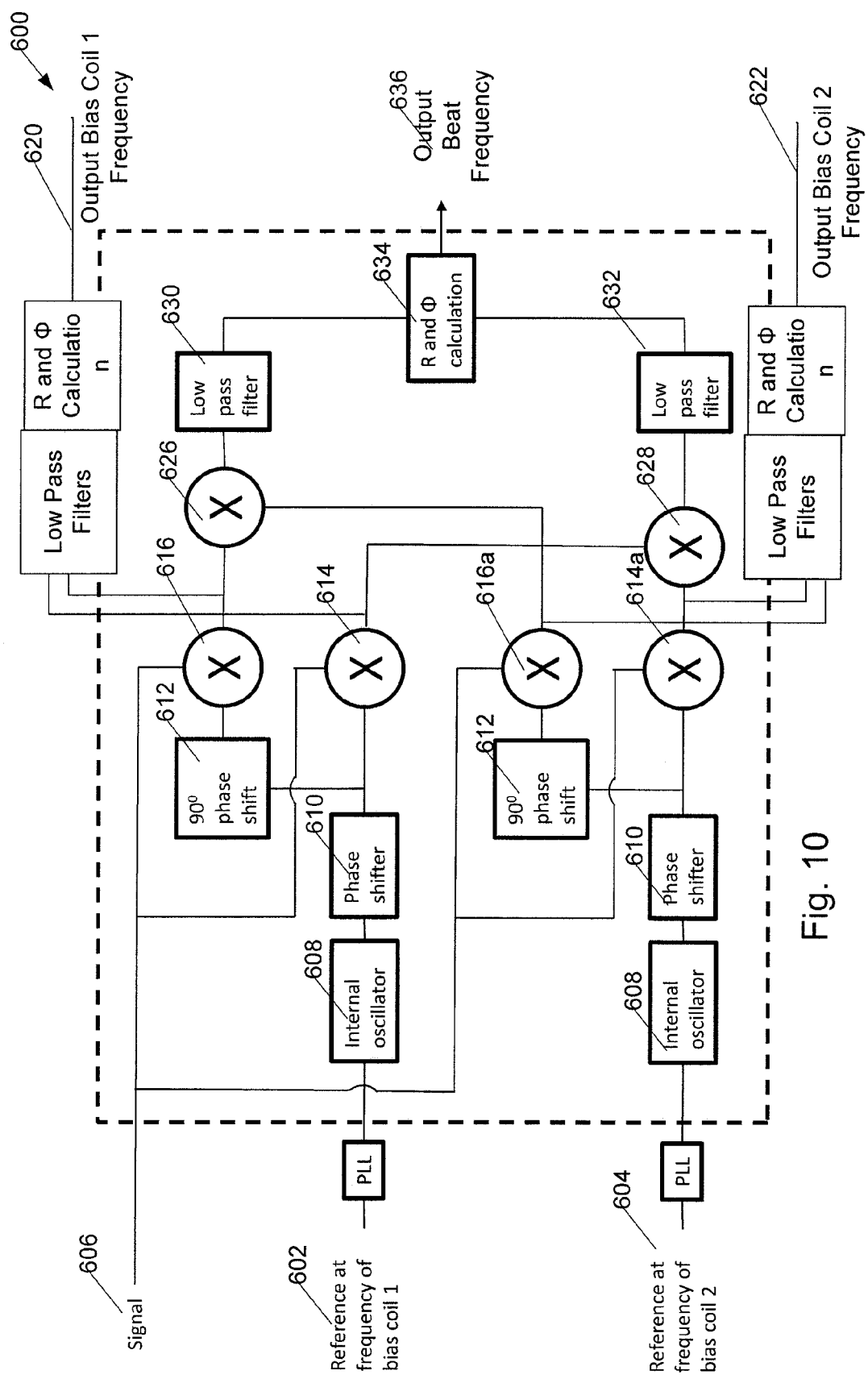
FIG. 10 illustrates a lock-in amplifier having outputs for signals detected at two reference frequencies and a beat frequency.

A lock-in amplifier 600 having the ability to detect signals at two reference frequencies and at a beat frequency is illustrated in FIG. 10, this amplifier may be implemented in analog or digital signal processing hardware. A first reference frequency input 602 and a second reference frequency input 604 are provided, the reference frequencies correspond to bias coil frequencies. In this amplifier, the reference frequencies are conditioned by phase locked loops 608, phase shifters 610, and 90-degree phase shifters 612. The input signal 606 is multiplied by outputs of phase shifters 610 in multipliers 614 for both first and second (614a) reference frequencies. Similarly, the input signal 606 is multiplied by outputs of 90-degree phase shifters 612 in multipliers 616 for both first and second 616a reference frequencies. As with the single-channel lock-in amplifier illustrated in FIG. 5A, the outputs of first-reference frequency multipliers 614, 616 are low-pass filtered and processed to determine outputs 620 representing magnitude and phase of input 606 components at the first reference frequency. Similarly, the outputs of second reference frequency multipliers 614a, 616a are low-pass filtered and processed in an amplitude and phase detector to determine outputs 622 representing magnitude and phase of input 606 components at the second reference frequency. Each of the first and second outputs 620, 622 resembles an output of a single-channel lock-in amplifier.

This amplifier then combines signals from both reference channels by multiplying the outputs of multipliers 616 and 616a in multiplier 626, and the output of multipliers 614, 614a in multiplier 628 to get signals incorporating components of both reference frequencies and the square of the input signal 606; these signals are low pass filtered in filters 630, 632 and processed in amplitude and phase detector 634 to give an output 636 representing input signal components at a beat frequency representative of a sum and/or difference of the first 602 and second 604 reference frequencies.

Tagging

Objects may be tagged with magnetic nanoparticles in one of two ways, through embedding in the object a particular size distribution of nanoparticles, as illustrated in FIG. 11A, where an object 1000 has embedded within it small nanoparticles 1002, mid-sized nanoparticles 1004, and large nanoparticles 1006, each in a particular concentration. In an embodiment, two bits of a binary identifier are encoded with each size of nanoparticle, with 00 represented by absence of particles of that size, 01 a small concentration, 10 a midsized concentration, and 11 a large concentration. With three sizes of nanoparticles, a 6-bit code is encoded. It is anticipated that additional concentrations and additional particle sizes can be used, thereby increasing the number of usable bits beyond six.

In an alternative embodiment, an object is tagged through positioning nanoparticle concentrations in a particular spatial distribution within the object 1020, as illustrated in FIG. 11B. The nanoparticles may be organized as bars in a single-dimensional bar-coded distribution, in a two-dimensional grid pattern as illustrated in FIG. 11B with a binary bit of a code represented by presence or absence of nanoparticles at a particular location, or in a three-dimensional array pattern. In an embodiment, nanoparticles present at a location 1022 represent a binary 1, and absent at a location 1024 represent a binary 0 of an object identification code.

In an alternative embodiment, additional information is encoded in an object by using two or more nanoparticle material compositions in conjunction with the size and concentration encoding illustrated in FIG. 11A and the spatial distribution encoding illustrated in FIG. 11B. For example, magnetic nanoparticles may be formulated from iron (II,III) oxide known as magnetite (Fe3O4), and magnetic nanoparticles may also be formulated from iron (III) oxides such as gamma phase maghemite (γ-Fe2O3), where the magnetic susceptibility properties of these two formulations are different and distinguishable using the MST system or the simplified system of FIG. 13. In an embodiment, nanoparticles identified to be magnetite represent a binary 1, and nanoparticles identified to be maghemite represent a binary 0 of an object identification code.

The MST system above described is usable to detect and map one, two, and three dimensional patterns of magnetic nanoparticles in an object, such as one tagged in accordance with FIG. 11B, thereby serving as a detector for patterns of magnetic nanoparticle taggants in an object. Similarly, the MST system is capable of detecting nanoparticle size distributions and detecting nanoparticle material compositions, so is also capable of serving as a detector for objects tagged with nanoparticle concentrations as described with reference to FIG. 11A.

In the presence of an applied magnetic field, the AC susceptibility response of magnetic nanoparticles has in-phase and out-of-phase components that vary as a function of frequency, particle domain size, material composition and temperature. This makes it possible to retrieve information encoded in a bulk material by adjusting the ratio of various particle size distributions as illustrated in FIG. 11A. This information can be retrieved from any point in the material with a simplified multi-frequency AC susceptometry reader 1050, as illustrated in FIG. 12, that is significantly simpler than a full MST machine. The reader has an adjustable, multifrequency, coil driver 1056 coupled to drive bias coils 1052, 1054 that flank a sensitive magnetic detector 1058. Data from magnetic detector 1058 is passed to a processor 1060 that also controls the coil driver 1056. For example, it is possible to make a magnetic nanoparticle credit card with its number, or a validation code, encoded in a nanoparticle size distribution that is mixed uniformly throughout the plastic. In an embodiment, processor 1060 contains firmware for driving the coil driver, taking data from the detector, determining a nanoparticle distribution, determining whether the nanoparticle distribution meets predetermined criteria for specific code elements such as binary bits or bit pairs, and, in an embodiment, for determining whether the specific code elements match an expected or valid code. In alternative embodiment, processor 1060 contains firmware for driving the coil driver, taking data from the detector, determining a nanoparticle distribution, determining whether the nanoparticle distribution meets predetermined criteria for specific code elements such as binary bits or bit pairs, and looks up the code in a small database to determine a product identity.

Figure 13:
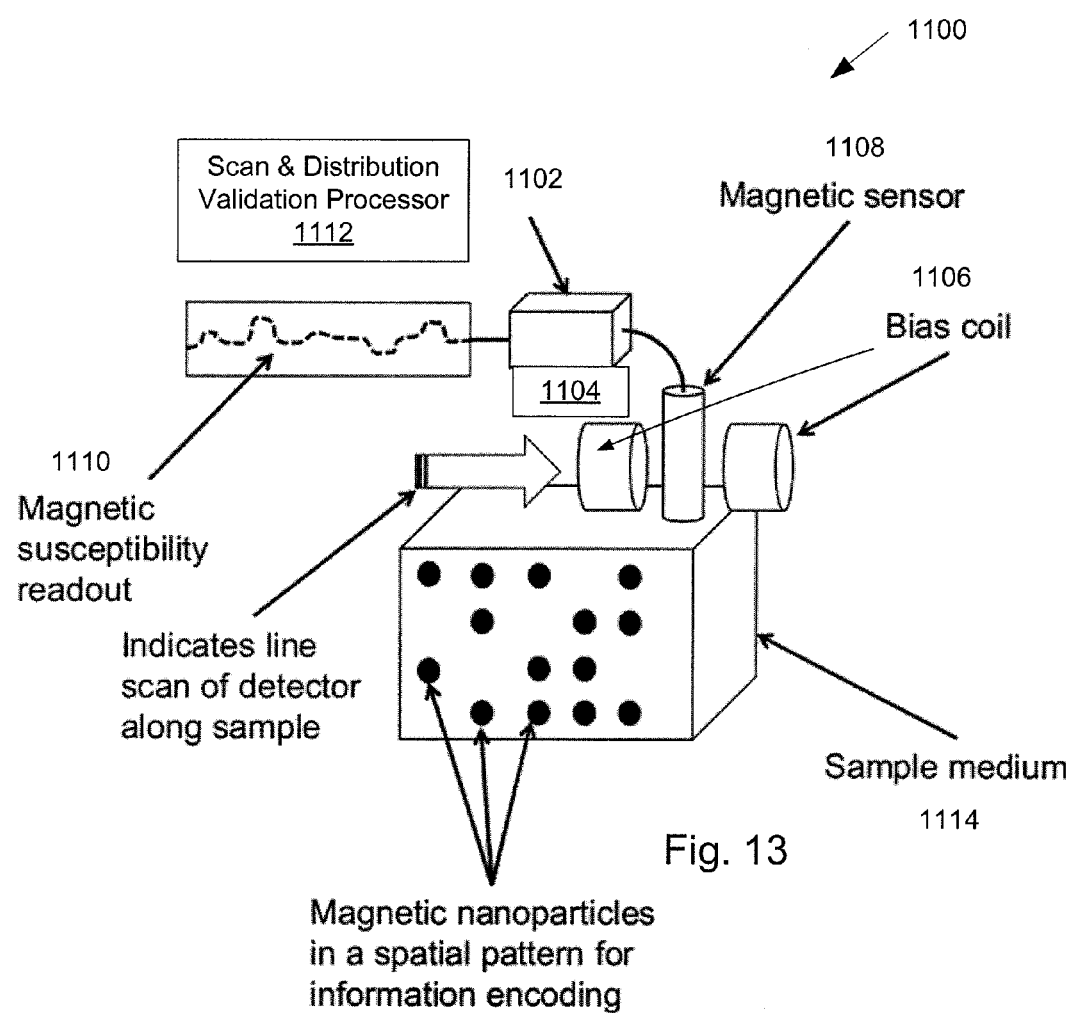
FIG. 13 is a schematic representation of a simplified single-or-dual axis detection and nanoparticle-distribution-mapping device for nanoparticles in an object tagged with a nanoparticle location distribution according to FIG. 11B.

A simplified reader capable of reading a one or two dimensional pattern of magnetic nanoparticle distributions as discussed with reference to FIG. 11B is illustrated in FIG. 13. In this reader, processor 1102 controls and configures coil driver 1104 to drive bias coils 1106 with an AC field perpendicular to sensor 1108, and reads sensor 1108 to provide a measure of magnetic susceptibility 1110. A mechanical scanner, not shown for simplicity, operates to scan object 1114 surface under control of a second processor, a scan-control and distribution processor 1112, having firmware for assigning magnetic susceptibility readings 1110 to specific locations, verifying whether the magnetic susceptibility readings meet predetermined criteria and thus correspond to presence or absence of taggant at each location, and whether the taggant meets predetermined criteria for specific code elements such as binary bits or bit pairs, and verifying presence or absence of a valid code.

It is also possible to combine spectroscopic and spatial encoding. These features make the magnetic nanoparticle taggant approach far more robust than traditional magnetic ink for non-destructive inspection and anti-counterfeit applications. The reader resembles that of FIG. 13.

New component fabrication methods such as 2D and 3D printing may also benefit from the magnetic nanoparticle taggant method. Photopolymers used in additive manufacturing processes like stereolithography may embed low concentrations of nanoparticle taggants. The proposed use of superparamagnetic nanoparticles has distinct advantages over conventional magnetic inks and magnetic strips. Conventional magnetic encoding uses multi-domain ferromagnetic materials that can be magnetized to encode information but can also be demagnetized. Single domain magnetic nanoparticles are superparamagnetic so they have a strong magnetization response in the presence of an applied field but there is no residual magnetization. This means that the signature cannot be removed from the material or read with a conventional magnetic reader. There is also no residual magnetization to possibly interfere with sensitive components like integrated circuits. Tagging with magnetic nanoparticles is important in non-conducting (i.e., insulating) materials such as polymers, ceramics, and composites that are used in critical applications in aerospace, civil infrastructure, industrial and consumer products.

The term processor has been used to describe digital signal processor and image processor 124. The term processor as used herein a single processor or a homogeneous or heterogeneous multiple processor system having one or more memories containing machine readable instructions configured to direct one or more processors of the processor system to perform the specific tasks described herein. In particular, it is anticipated that processor 124 may include multiple processors each configured to perform one or another specific task, the multiple processors cooperating to perfolin MST imaging, taggant detection, or contrast agent detection and localization.

Combinations

The various elements herein described may be combined in many ways. Among many anticipated combinations of elements are An apparatus designated A for obtaining magnetic susceptibility data includes multiple sensitive magnetic sensors disposed about a measurement volume, and adapted to measure magnetic fields of the measurement volume; multiple bias coils disposed about the measurement volume and adapted for providing magnetic fields within the measurement volume; driving circuitry coupled to the bias coils and adapted to driving the bias coils with alternating current; sensing circuitry coupled to read the sensitive magnetic sensors; digitization circuitry adapted to digitize readings of the sensitive magnetic sensors; a processor adapted to receive information from the digitization circuitry; magnetic susceptibility tomography (MST) routines in memory of the processor, the MST routines comprising machine readable instructions for directing the processor to divide the measurement volume into voxels, to determine differences between applied and measured field strengths of magnetic fields at each sensor, to determine a value at each voxel selected from the group consisting of a contribution of difference between applied and measured strengths of magnetic fields and a magnetic susceptibility, and to construct tomographic images based on those values as MST images.

Apparatus designated AA including the apparatus designated A wherein the driving circuitry is adapted for driving at least a first, a second, a third, and a fourth of the bias coils with AC current at a first, a second, a third, and a fourth respective frequency.

Apparatus designated AAA including the apparatus designated A or AA wherein the driving circuitry is adapted for time multiplexing the frequencies that are supplied to at least the first, second, third and fourth coils of the bias coils.

Apparatus designated AB including the apparatus designated AA further including lock-in amplifiers coupled to amplify signals from the sensitive magnetic sensors, the lock-in amplifiers coupled to the digitization circuitry.

Apparatus designated AC including the apparatus designated AB wherein the lock-in amplifiers are digital lock-in amplifiers configured to receive signals from the sensors through the digitization circuitry.

Apparatus designated ABA wherein the lock-in amplifiers are analog lock-in amplifiers configured to amplify signals from the sensors and having outputs coupled to the digitization circuitry.

Apparatus designated AD including the apparatus designated A, AA, AAA, AB, AC, or ABA wherein the sensing circuitry is coupled to read current in the bias coils, and wherein the system correlates current in the bias coils to measured magnetic fields measured by the magnetic sensors to determine applied and measured field strengths of magnetic fields.

Apparatus designated AE including the apparatus designated AD wherein the correlation of current in the bias coils to measured magnetic fields is performed by linear regression.

Apparatus designated AF including the apparatus designated A, AA, AAA, AB, ABA, AC, AD, or AE wherein at least a first and a second of the bias coils are driven at different frequencies and wherein the memory of the processor further includes correlation routines for extracting contributions of each bias coil to each sensor, and for rejecting noise.

Apparatus designated AG including the apparatus designated A, AA, AAA, AB, ABA, AC, AD, AE, or AF wherein the MST routines are adapted to determine a contribution of magnetic fields from each of at least the first, second, third, and fourth bias coils to measured magnetic fields at each of at least a first and a second sensor of the sensitive magnetic sensors.

Apparatus designated AH including the apparatus designated A, AA, AAA, AB, ABA, AC, AD, AE, AF, AG wherein data from the sensitive magnetic sensors is filtered by low pass filters having a cutoff frequency below the first, second, third, and fourth frequencies to provide magnetoencephalographic data.

Apparatus designated AI including the apparatus designated A, AA, AAA, AB, AC, AD, AE, AF, AG, or AH further comprising magnetoencephalographic tomography (MET) routines in memory of the processor, the MET routines comprising machine readable instructions for directing the processor to divide the measurement volume into voxels, to determine magnetic field strength contributions from each voxel from the magnetoencephalographic data, and to construct tomographic images displaying those magnetic fields contributions as MET images.

Apparatus designated AJ including the apparatus designated A, AA, AAA, AB, AC, AD, AE, AF, AG, AH, or AI further comprising composite tomography routines in memory of the processor.

Apparatus designated AK including the apparatus designated A, AA, AAA, AB, AC, AD, AE, AF, AG, AH, AI, or AJ wherein the apparatus is adapted to determine magnetic susceptibility data from a head of a subject.

Apparatus designated AL including the apparatus designated A, AA, AAA, AB, AC, AD, AE, AF, AG, AH, AI, AJ, AK wherein the system is adapted for reading MST data sufficiently fast to provide an MST sequence of at least several frames per minute.

Apparatus designated AM including the apparatus designated A, AA, AAA, AB, AC, AD, AE, AF, AG, AH, AI, AJ, AK, or AL wherein the MST sequence has an effective frame rate of at least five hertz.

Apparatus designated AN including the apparatus designated A, AA, AAA, AB, AC, AD, AE, AF, AG, AH, AI, AJ, AK, AL, or AM wherein the sensitive magnetic sensors are SQUID sensors.

Apparatus designated AO including the apparatus designated A, AA, AAA, AB, AC, AD, AE, AF, AG, AH, AI, AJ, AK, AL, or AM wherein the sensitive magnetic sensors are atomic magnetometers.

Apparatus designated AP including the apparatus designated A, AA, AAA, AB, AC, AD, AE, AF, AG, AH, AI, AJ, AK, AL, or AM wherein the sensitive magnetic sensors are fluxgate sensors.

Apparatus designated AQ including the apparatus designated A, AA, AAA, AB, AC, AD, AE, AF, AG, AH, AI, AJ, AK, AL, or AM wherein the sensitive magnetic sensors are induction coils.

Apparatus designated AR including the apparatus designated A, AA, AAA, AB, AC, AD, AE, AF, AG, AH, AI, AJ, AK, AL, or AM wherein the sensitive magnetic sensors are Hall effect sensors.

Apparatus designated AS including the apparatus designated A, AA, AAA, AB, AC, AD, AE, AF, AG, AH, AI, AJ, AK, AL, or AM wherein the sensitive magnetic sensors are magnetoresistive sensors.

Apparatus designated AT including the apparatus designated A, AA, AAA, AB, AC, AD, AE, AF, AG, AH, AI, AJ, AK, AL, or AM further comprising magnetic nanoparticles injected into the subject.

Apparatus designated AU including the apparatus designated A, AA, AAA, AB, AC, AD, AE, AF, AG, AH, AI, AJ, AK, AL, AM or AT and further including a plurality of compensation coils coupled to be driven by a plurality of compensation coil drivers, the compensation coil drivers coupled to the processor, wherein the processor comprises machine readable instructions for controlling the compensation coils to cancel bias fields at the sensors.

Apparatus designated AV including the apparatus designated A, AA, AAA, AB, AC, AD, AE, AF, AG, AH, AI, AJ, AK, AL, AM, AT, or AU and further including an ambient field sensor and ambient-field compensation magnets coupled to be driven to cancel ambient magnetic fields at the measurement volume.

A method designated B of producing magnetic susceptibility tomographic (MST) images of an object includes providing an alternating magnetic field to a volume of an object from at least a first bias coil at a first frequency, a second bias coil at a second frequency, a third bias coil at a third frequency, and a fourth bias coil at a fourth frequency, the first, second, third, and fourth frequencies being different; measuring magnetic fields at a plurality of sensors disposed about the volume; constructing a model in memory of a processor, the model having multiple voxels representative of smaller volumes within the volume; correlating currents of the bias coils to measured magnetic fields at each sensor of the plurality of sensors to determine an applied and an induced magnetic field at each sensor; deriving magnetic susceptibility information for each voxel; and producing an MST image indicative of magnetic susceptibility at voxels.

A method designated BA including the method designated B and further including determining magnetoencephalographic tomographic information.

A method designated BB including the method designated B or BA wherein the sensors are SQUID sensors.

A method designated BC including the method designated B or BA wherein the sensors are atomic magnetometers.

A method designated BD including the method designated B or BA wherein the sensors are fluxgate sensors.

A method designated BE including the method designated B or BA wherein the sensitive magnetic sensors are induction coils.

A method designated BF including the method designated B or BA wherein the sensitive magnetic sensors are selected from the group consisting of Hall effect sensors and magnetoresistive sensors.

A method designated BG including the method designated B, BA, BB, BC, BD, BE, or BF wherein the step of measuring magnetic fields includes inputting a signal from a first sensor to a first lock-in amplifier having a reference signal at the first frequency, and inputting a signal from a second sensor to a second lock-in amplifier having a reference signal at the second frequency.

A method designated BH including the method designated BG and further including inputting a signal from the first sensor to a third lock-in amplifier having two reference signals at each of the first and second frequencies to amplify the signal carried on the beat frequency between the first and second frequencies.

A method designated BI including the method designated B, BA, BB, BC, BD, BE, BF, BG, or BH and further including adding a taggant or contrast agent comprising magnetic nanoparticles to the object.

A method designated BJ including the method designated BI wherein the at least one taggant or contrast agent is added to at least one region of the object and a second one taggant or contrast agent comprising magnetic nanoparticles is added to at least a second region, A method designated BK including the method designated B, BA, BB, BC, BD, BE, BF, BG, BH, or BI wherein the object is a living mammal.

A method designated BK including the method designated B, BA, BB, BC, BD, BE, BF, BG, BH, or BI where the object is a human subject.

A method designated BK including the method designated B, BA, BB, BC, BD, BE, BF, BG, BH, or BI wherein the object is nonliving, and the nanoparticles form an object recognition code.

An apparatus designated C for obtaining magnetic susceptibility data from an object including at least one sensitive magnetic sensor disposed near the object, and adapted to measure magnetic fields of the object; a plurality of bias coils disposed near the object and adapted for providing magnetic fields within the object; driving circuitry coupled to the bias coils and adapted to driving the bias coils with alternating current; sensing circuitry coupled to read the sensitive magnetic sensor; digitization circuitry adapted to digitize readings of the sensitive magnetic sensor; a processor adapted to receive information from the digitization circuitry; magnetic susceptibility taggant recognition (MSTR) routines in memory of the processor, the MSTR routines comprising machine readable instructions that when executed determine differences between applied and measured field strengths of magnetic fields at each sensor, to determine a response comprising a contribution of difference between applied and measured strengths of magnetic fields at a plurality of frequencies and a frequency distribution of magnetic susceptibility, and to recognize a taggant in the object when the response meets predetermined criteria.

An apparatus designated CA including the apparatus designated C wherein the taggant comprises a blend of at least two different size distributions of nanoparticles, An apparatus designated CB including the apparatus designated C or CA wherein the taggant comprises a blend of at least two different material compositions of nanoparticles.

An apparatus designated CC including the apparatus designated C, CA, or CB further comprising firmware for determining a binary code from at least one of taggant locations, taggant nanoparticle size distributions, taggant concentrations, and taggant material composition.

CONCLUSION

It should thus be noted that the matter contained in the above description or shown in the accompanying drawings should be interpreted as illustrative and not in a limiting sense. The following claims are intended to cover generic and specific features described herein, as well as all statements of the scope of the present method and system.

What is claimed is:

1. An apparatus for obtaining magnetic susceptibility data comprising:
    a plurality of sensitive magnetic sensors disposed about a measurement volume, and adapted to measure magnetic fields of the measurement volume;
    a plurality of bias coils disposed about the measurement volume and adapted for providing bias magnetic fields within the measurement volume;
    driving circuitry coupled to the bias coils and adapted to driving the bias coils with alternating current;
    sensing circuitry coupled to read the sensitive magnetic sensors;
    digitization circuitry adapted to digitize readings of the sensitive magnetic sensors;
    a processor adapted to receive information from the digitization circuitry;
    magnetic susceptibility tomography (MST) routines configured in memory of the processor, the MST routines comprising machine readable instructions for directing the processor to divide the measurement volume into voxels, to determine differences between bias and measured field strengths of magnetic fields at each sensitive magnetic sensor, to determine a value at each voxel selected from the group consisting of a contribution of difference between bias and measured strengths of magnetic fields and a magnetic susceptibility, and to construct tomographic images based on those values as MST images.

2. The apparatus of claim 1 wherein the driving circuitry is adapted for driving at least a first, a second, a third, and a fourth of the bias coils with AC current at a first, a second, a third, and a fourth respective frequency.

3. The apparatus of claim 2 further comprising lock-in amplifiers coupled to amplify signals from the sensitive magnetic sensors, for extracting contributions of each bias coil to each sensor, and for rejecting noise, the lock-in amplifiers coupled to the digitization circuitry.

4. The apparatus of claim 3 wherein the lock-in amplifiers are digital lock-in amplifiers configured to receive signals from the sensitive magnetic sensors through the digitization circuitry.

5. The apparatus of claim 3 wherein the lock-in amplifiers are analog lock-in amplifiers configured to amplify signals from the sensitive magnetic sensors and having outputs coupled to the digitization circuitry.

6. The apparatus of claim 2 wherein the driving circuitry is adapted for time multiplexing the frequencies that are supplied to at least the first, second, third and fourth coils of the bias coils.

7. The apparatus of claim 1 wherein the sensing circuitry is coupled to read current in the bias coils, and wherein the system correlates current in the bias coils to magnetic fields measured by the sensitive magnetic sensors to determine bias and measured field strengths of the magnetic fields.

8. The apparatus of claim 7 wherein the correlation of current in the bias coils to measured magnetic fields is performed by linear regression.

9. The apparatus of claim 7 wherein at least a first and a second of the bias coils are driven at different frequencies and wherein the memory of the processor further includes correlation routines for extracting contributions of each bias coil to each sensitive magnetic sensor, and for rejecting noise.

10. The apparatus of claim 3, wherein data from the sensitive magnetic sensors is filtered by low pass filters having a cutoff frequency below the first, second, third, and fourth frequencies to provide biomagnetic data.

11. The apparatus of claim 3, further comprising magnetoencephalographic tomography (MET) routines in memory of the processor, the MET routines comprising machine readable instructions for directing the processor to divide the measurement volume into voxels, to determine magnetic field strength contributions from each voxel from the magnetoencephalographic data, and to construct tomographic images displaying those magnetic fields contributions as MET images.

12. The apparatus of claim 11 further comprising composite tomography routines in memory of the processor.

13. The apparatus of claim 3, wherein the apparatus is adapted to determine magnetic susceptibility data from a head of a subject.

14. The apparatus of claim 13 wherein the apparatus is adapted for reading MST data sufficiently fast to provide an MST sequence of at least several frames per minute.

15. The apparatus of claim 14 wherein the MST sequence has an effective frame rate of at least five hertz.

16. The apparatus of claim 3, wherein the sensitive magnetic sensors are superconducting quantum interference device (SQUID) sensors.

17. The apparatus of claim 3, wherein the sensitive magnetic sensors are atomic magnetometers.

18. The apparatus of claim 3, wherein the sensitive magnetic sensors are fluxgate sensors.

19. The apparatus of claim 3, wherein the sensitive magnetic sensors are induction coils.

20. The apparatus of claim 3, wherein the sensitive magnetic sensors are Hall effect sensors.

21. The apparatus of claim 3, wherein the sensitive magnetic sensors are magnetoresistive sensors.

22. The apparatus of claim 3, further comprising magnetic nanoparticles injected into the measurement volume.

23. The apparatus of claim 3, comprising a plurality of compensation coils coupled to be driven by a plurality of compensation coil drivers, the compensation coil drivers coupled to the processor, wherein the processor comprises machine readable instructions for controlling the compensation coils to cancel bias fields at the sensors.

24. The apparatus of claim 23 further comprising an ambient field sensor and ambient-field compensation magnets coupled to be driven to cancel ambient magnetic fields at the measurement volume.

25. A method of producing magnetic susceptibility tomographic (MST) images of an object comprising:
- providing an alternating magnetic field to a volume of the object from at least a first bias coil at a first frequency, a second bias coil at a second frequency, a third bias coil at a third frequency, and a fourth bias coil at a fourth frequency, the first, second, third, and fourth frequencies being different;
- measuring magnetic fields at a plurality of sensors disposed about the volume;
- constructing a model in memory of a processor, the model having multiple voxels representative of smaller volumes within the volume;
- relating currents of the bias coils to bias fields at each voxel represented in the model and bias fields at each sensor of the plurality of sensors;
- relating the effects of magnetic susceptibility at the voxels on a measured magnetic field at each sensor;
- deriving magnetic susceptibility information for each voxel from the modeled relationships between the bias fields, magnetic susceptibility at the voxels and measured magnetic fields; and
- producing an MST image indicative of magnetic susceptibility at voxels.

26. The method of claim 25, further comprising relating the magnetic fields of contributed by compensation coils at each voxel and at each sensor of the plurality of sensors when deriving magnetic susceptibility information for each voxel represented in the model and producing an MST image.

27. The method of claim 26, further comprising determining magnetoencephalographic tomographic information from the derived susceptibility information for each voxel.

28. The method of claim 25, wherein the sensors are SQUID sensors.

29. The method of claim 25, wherein the sensors are atomic magnetometers.

30. The method of claim 25, wherein the sensors are fluxgate sensors.

31. The method of claim 25, wherein the sensors are induction coils.

32. The method of claim 25, wherein the sensors are selected from the group consisting of Hall effect sensors and magnetoresistive sensors.

33. The method of claim 26 wherein the step of measuring magnetic fields includes inputting a signal from a first sensor to a first lock-in amplifier having a reference signal at the first frequency, and inputting a signal from a second sensor to a second lock-in amplifier having a reference signal at the second frequency.

34. The method of claim 33 further comprising inputting a signal from the first sensor to a third lock-in amplifier having two reference signals at each of the first and second frequencies to amplify the signal carried on the beat frequency between the first and second frequencies.

35. The method of claim 30, further comprising adding a taggant or contrast agent comprising magnetic nanoparticles to the object.

36. The method of claim 35 wherein the at least one taggant or contrast agent is added to at least one region of the object and a second one taggant or contrast agent is added to at least a second region.

37. The method of claim 35 wherein the object is a living mammal.

38. The method of claim 35 where the object is a human subject.

39. The method of claim 35 wherein the object is nonliving, and the nanoparticles form an object recognition code.

40. An apparatus for obtaining magnetic susceptibility data from an object comprising:
- at least one sensitive magnetic sensor disposed near the object, and adapted to measure magnetic fields of the object;
- a plurality of bias coils disposed near the object and adapted for providing magnetic fields within the object;
- driving circuitry coupled to the bias coils and adapted to driving the bias coils with alternating current;
- sensing circuitry coupled to read the sensitive magnetic sensors;
- digitization circuitry adapted to digitize readings of the sensitive magnetic sensors;
- a processor adapted to receive information from the digitization circuitry;
- magnetic susceptibility taggant recognition (MSTR) routines in memory of the processor, the MSTR routines comprising machine readable instructions that when executed determine differences between applied and measured field strengths of magnetic fields at each sensor, to determine a response comprising a contribution of difference between applied and measured strengths of magnetic fields at a plurality of frequencies and a frequency distribution of magnetic susceptibility, and to recognize a taggant in the object when the response meets predetermined criteria.

41. The apparatus of claim 40 wherein the taggant comprises a blend of at least two different size distributions of nanoparticles.

42. The apparatus of claim 40 wherein the taggant comprises a blend of at least two different material compositions of nanoparticles.

43. The apparatus of claim 40, further comprising firmware for determining a binary code from at least one or more of taggant locations, taggant concentrations, taggant nanoparticle size distributions, and taggant material composition.

* * * * *